United States Patent
Wachs et al.

(10) Patent No.: US 6,350,918 B2
(45) Date of Patent: Feb. 26, 2002

(54) ALCOHOL CONVERSION

(75) Inventors: Israel E. Wachs, Bridgewater, NJ (US); Yeping Cai, Louisville, KY (US)

(73) Assignee: Lehigh University, Bethlehem, PA (US)

( * ) Notice: Subject to any disclaimer, the term of this patent is extended or adjusted under 35 U.S.C. 154(b) by 0 days.

(21) Appl. No.: 09/835,575

(22) Filed: Apr. 17, 2001

Related U.S. Application Data

(62) Division of application No. 09/290,404, filed on Apr. 13, 1999, now Pat. No. 6,245,708.
(60) Provisional application No. 60/081,957, filed on Apr. 15, 1998.

(51) Int. Cl.$^7$ ............................................. C07C 45/29
(52) U.S. Cl. ...................... 568/471; 568/431; 568/449; 568/472; 568/487
(58) Field of Search ................................ 568/431, 449, 568/471, 472, 487

(56) References Cited

U.S. PATENT DOCUMENTS 5,345,010 A 9/1994 Lyons et al. ................. 568/910

OTHER PUBLICATIONS

Nakamura et al, Bull.Chem.Soc.Jpn., 68(3), 997–1000 (1995).*
Nakamura et al, Chem.Lett., (4) pp. 749–752 (1993).*
Topsoe, H. *Hydroprocessing:II. Fundamental Aspects*; Bonnelle, J. P. et al. (Eds.); D. Reidel Publishing Company, Boston, 1983; pp 329.
Bond, G. C.; Vedrine, J. C. *Catal. Today* 1994, 20, 1.
Centi, G. *Appl. Catal. A*, 1996, 147, 267.
Bosch, H.; Janssen, F. *Catal. Today* 1988, 2, 369.
Wachs, I. E. *Catalysis* 1997, 13, 37.
Haber, J. *Pure & Appl. Chem.* 1984, 56, 1663.
Xie, Y. C.; Tang, Y. Q. *Adv. Catal.* 1990, 31, 1.
Knozinger, H.; Taglauer, E. *Catalysis* 1993, 10, 1.
Wachs, I. E. *Catal. Today* 1996, 27, 457.
Gasior, M.; Haber, J.; Machej. T. *Appl. Catal.* 1987, 33, 1.
Cavalli, P.; Cavani, F.; Manenti, I.; Trifiro, F. *Ind. Eng. Chem. Res.* 1987, 26, 639.
Deo, G.; and Wachs; I. E. *J. Catal.* 1994, 146, 335.
Vuurman, M. A.; Hirt, A. M.; Wachs, I. E. *J. Phys. Chem.* 1991, 95, 9928.
Haber, J.; Machej, T.; Grabowski, R. *Solid State Ionics* 1989, 32/33, 887.
Xie, Y.; Gui, L.; Liu, Y.; Zhao B.; Yang, N.; Zhang, Y.; Guo, Q.; Duan L.; Huang, H.; Cai, X.; Tang, Y. *Proc. 8$^{th}$ Intern. Congr. Catal.*; Dechema, Frankfurt, and Verlag Chemie: Weinheim, 1984; vol. V, pp. 147.
Margraf, R.; Leyrer, J.; Taglauer, E.; Knozinger, H. *React. Kinet. Catal. Lett.* 1987, 35, 261.
Leyrer, J.; Margraf, R.; Taglauer E.; Knozinger H. *Surf. Sci.* 1988, 201, 603.
Machej, T.; Haber, J.; Turek A. M.; Wachs, I. E. *Appl. Catal.* 1991, 70, 115.
Haber, J. *Concepts In Catalysis by Transition Metal Oxides*; Bonnelle, J. P. et al. (Eds.); D. Reidel Publishing Company, Boston, 1983; pp 1–45.
Haber, J.; Machej, T.; Czeppe, T. *Surf. Sci.* 1985, 151, 301.
Honicke, D.; Xu, J. *J. Phys. Chem.* 1988, 92, 4699.
Hausinger, G.; Schmelz, H.; Knozinger, H. *Appl. Catal.* 1988, 39, 267.
Hu, H.; Wachs, I. E. *J. Phys. Chem.* 1995, 99, 10911.
Stampfl, S. R.; Chen, C.; Dumesic, J. A.; Niu, C.; Hill, Jr., C. G. *J. Catal.* 1987, 105, 445.
Jehng, J. M.; Hu, H.; Gao, X., Wachs, I. E. *Catal. Today* 1996, 28, 335.
Wachs, I. E.; Jehng, J. M.; Deo, G.; Weckhuysen, B. M.; Guliants, V. V.; Benziger, J.B. Catal. Today 1996, 32, 47.
Went, G.; Oyama, S. T.; Bell, A. T. *J. Phys. Chem.* 1990, 94, 4240.
Eckert, H.; Wachs, I.E. *J. Phys. Chem.* 1989, 93, 6796.
Hardcastle, F. D.; Wachs, I.E. *J. Mol. Catal.* 1988, 46, 173.
Vuurman, M. A.; Wachs, I. E.; Stufkens, D. J.; Oskam, A. *J. Mol. Catal.* 1993, 80, 209.
Hardcastle, F. D.; Wachs, I. E. *J. Mol. Catal.* 1988, 46, 15.
Jehng, J.M.; Wachs, I. E. *Catal. Today* 1993, 16, 417.
Deo, G.; Wachs, I. E. *J. Phys. Chem.* 1991, 95, 5889.
Kim, D.S.; Ostromecki, M.; Wachs, I. E. *J. Mol. Catal. A* 1996, 106, 93.
Ruckenstein, E.; Lee, S. H. *J. Catal.* 1987, 104, 259.
Wanke, S. E.; Flynn, P. C. *Catal. Rev. Sci. Eng.* 1975, 12, 93.
Wang, C. B.; Xie, Y. C.; Tang, Y. Q. *Science in China* 1994, 37, 1458.
Haber, J.; Machej, T.; Serwicka, E. M.; Wachs, I. E. *Catal. Lett.* 1995, 32, 101.
Margraf, R.; Leyrer, J.; Taglauer, E.; Knozinger, H. *Surface Sci.* 1987, 189/190, 842.
Leyrere, J.; Zaki, M. I.; Knozinger, H. *J. Phys. Chem.* 1986, 90, 4775.
Leyrer, J.; Mey, D.; Knozinger, H. *J. Catal.* 1990, 124, 349.
Shan, S.; Honicke, D. *Chem.–Ing.–Techn.* 1989, 61, 321.
Cheng, W. H. *J. Catal.* 1996, 158, 477.
Holstein, W.; Machiels, C. J. *J. Catal.* 1996, 162, 118.
Segawa, K.; Hall, W. K. *J. Catal.* 1982, 77, 221.
Turek, A. M.; Wachs, I. E.; DeCanio, E. J. Phys. Chem. 1992, 96, 5000.

(List continued on next page.)

*Primary Examiner*—Sreeni Padmanabhan
(74) *Attorney, Agent, or Firm*—Banner & Witcoff, Ltd.

(57) ABSTRACT

Preparing an aldehyde from an alcohol by contacting the alcohol in the presence of oxygen with a catalyst prepared by contacting an intimate mixture containing metal oxide support particles and particles of a catalytically active metal oxide from Groups VA, VIA, or VIIA, with a gaseous stream containing an alcohol to cause metal oxide from the discrete catalytically active metal oxide particles to migrate to the metal oxide support particles and to form a monolayer of catalytically active metal oxide on said metal oxide support particles.

19 Claims, 26 Drawing Sheets

OTHER PUBLICATIONS

Bradley, D. C.; Mehrotra, R.C.; Gaur, D. P. *Metal Alkoxides*; Academic Press: New York, 1978.

Farneth, W. E.; Staley, R. H.; Sleight, A. W. *J. Am. Chem. Soc.* 1986, 108, 2327.

Knozinger, H. *Mater. Sci. Forum*, 1988, 25/26, 223.

Jehng, J. M.; Wachs, I. E.; Weckhuysen, B. M.; Schoonheydt, R. A. *J. Chem. Soc. Faraday Trans.* 1995, 91, 953.

Deo, G; Turek, A. M.; Wachs, I. E.; Machej, T.; Haber, J.; Das, N.; Eckert, H.; Hirt, A. M. *Appl. Catal. A* 1992, 91, 27.

Fouad, N. E.; Knozinger, H.; Ismail H. M.; Zaki, M. I. Z. *Phys. Chem.* 1991, 173, 201.

Tatibouet, J. M. *Appl. Catal.* A 1997, 148, 213.

Ruiz, P.; Delmon, B. *Catal. Today* 1988, 3, 199.

Delmon, B.; Froment, G. F. *Catal. Rev.–Sci. Eng.* 1996, 38, 69.

Centi, G.; Pinelli, D.; Trifiro, F.; Ghoussoub, G.; Guelton, M.; Gengembre, L. *J. Catal.* 1991, 130, 238.

Pearce, R.; Patterson, W. R. *Catalysis and Chemical Process*; Wiley: New York, 1981.

Banares, M.; Hu, H.; Wachs, I. E. *J. Catal.* 1994, 150, 407.

\* cited by examiner

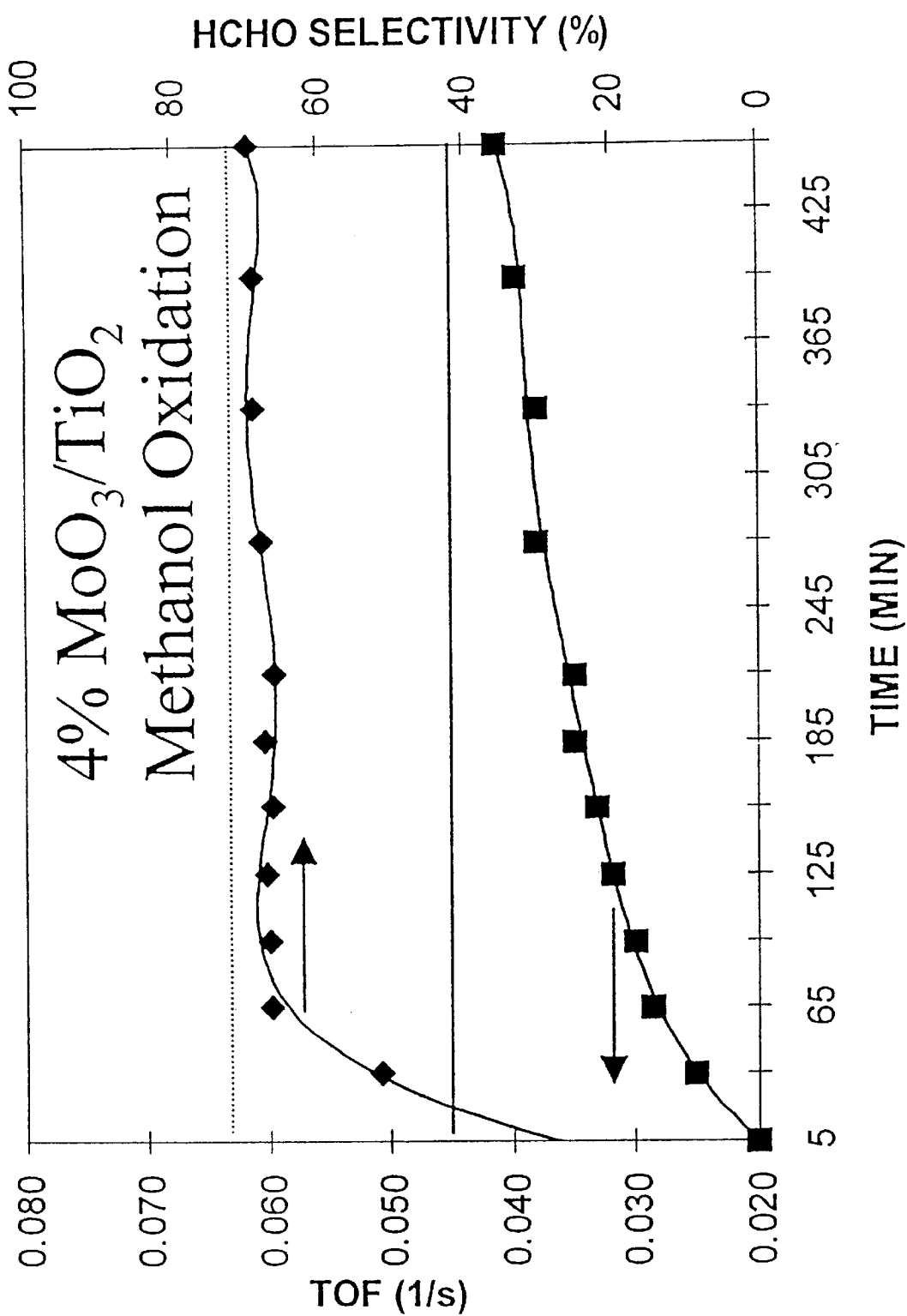
FIG. 8(A) 4% MoO₃/TiO₂ Methanol Oxidation

ALCOHOL CONVERSION

This application is a divisional application of Ser. No. 09/290,404, filed Apr. 13, 1999, now U.S. Pat. No. 6,245,708 which claims the priority benefits from the U.S. provisional application Serial No. 60/081,957 filed Apr. 15, 1998.

Financial support has been provided by the Division of Basic Energy Sciences of the Department of Energy, grant DEFG02-93ER 14550.

FIELD OF THE INVENTION

The present invention is directed to a catalyst composition, its method of preparation, and a process for using the composition for alcohol oxidation to the corresponding aldehydes.

BACKGROUND OF THE INVENTION

The surface metal oxide species on oxide supports play a crucial role in the catalytic processes of supported metal oxide catalysts, which have been widely used as catalysts in numerous industrial applications: $MoO_3/g—Al_2O_3$ and $WO_3/g—Al_2O_3$ catalysts for hydrodesulfurization (HDS) and hydrodenitrogenation (HDN),[1-2] $V_2O_5/TiO_2$ catalysts for o-xylene oxidation to phthalic anhydrid[3,4] and selective catalytic reduction (SCR) of $NO_x$.[5] The industrial development of supported metal oxide catalysts over the past five decades has been summarized in a recent review paper.[6]

Fundamental information about the surface metal oxide molecular structures have been obtained by a battery of physical and chemical techniques, including Raman spectroscopy, infrared spectroscopy (IR), X-ray photoelectron spectroscopy (XPS), UV diffuse reflectance spectroscopy (UV-vis), solid-state nuclear magnetic resonance (NMR), extended X-ray absorption fine structure (EXAFS), Mossbauer spectroscopy, surface acidity, adsorption, and probe reactions.[7-10] The reactivity of the surface metal oxide species in various supported metal oxide catalysts has been probed by different chemical reactions including methanol oxidation, alkane oxidation, $SO_2$ oxidation, and the selective catalytic reduction of $NO_x$.[6] Correlation of the catalytic reactivity with the corresponding molecular structural information about the surface metal oxide species has elucidated many fundamental issues about the catalytic properties of the surface metal oxide species during catalytic reactions: the roles of terminal double bonds, bridging bonds, adjacent or neighboring sites, secondary metal oxide additives, support ligands, and preparation methods. The fundamental information obtained from these molecular structure-reactivity relationships has great potential for the molecular design and engineering of supported metal oxide catalysts for various catalytic applications.

The formation of a two-dimensional metal oxide species on surfaces of oxide supports through thermal spreading of three-dimensional bulk metal oxides (schematically represented in FIG. 1) is well documented in the catalysis literature.[7,8] Thermal spreading is a spontaneous process from a thermodynamics perspective. However, its kinetics are constrained and require a high temperature for surface diffusion or migration of one metal oxide component over the surface of a secondary oxide support to occur at an appreciable rate. In the context of thermal spreading, Tammann temperature ($T_{Tam} >> 0.5 T_{mp}$; $T_{mp}$=bulk melting point of the dispersed metal oxide) is often used to estimate the temperature for thermal treatments. The driving force for thermal spreading and formation of the surface metal oxide monolayer is a concentration gradient of the dispersed component or a decrease in the overall system surface free energy.

In contrast, little information is available on the spreading of metal oxides over oxide supports during catalytic reactions. Gasior et al.[11] previously reported the spreading of vanadia over the surface of $TiO_2$ (anatase) grains in a $V_2O_5$ and $TiO_2$ (anatase) physical mixture during o-xylene oxidation at 360° C., which was manifested by increase in both conversion and phthalic anhydride selectivity with reaction time. Cavalli et al. earlier observed that soluble bulk $V_2O_5$ spreads over the free rutile surface and, on the contrary, the insoluble vanadium oxide partly segregates and forms the soluble bulk $V_2O_5$, during ammoxidation of toluene to benzonitrile at 320–390° C.[12] However, the reaction temperatures (~360° C.) were much higher than the Tammann temperature (210° C.) of crystalline $V_2O_5$, implying that thermal spreading might have dominated the spreading kinetics during the reaction.

BRIEF SUMMARY OF THE INVENTION

It has now been discovered that catalysts useful for producing aldehydes from alcohols contain a physical mixture comprising: (a) a particulate source of a metal oxide support, and (b) a source of metal oxidation catalyst selected from the group consisting of oxides of group VA, VIA, and VIIA metals that are catalytically active for alcohol conversion to aldehydes. During the course of the conversion reaction, a catalytically active monolayer of the VA, VIA, or VIIA metal oxides migrates to surfaces of the metal oxide support particles and form supported, catalytically active compositions with enhanced selectivity and activity for the conversion reaction.

Catalysts formed by the present invention and the resulting alcohol conversion process are comparable to prior art catalysts formed via the more expensive alkoxide impregnation manufacturing methods of the prior art. These and other advantages will be readily recognized by those of skill in the art.

A method for forming a catalytically active composition in accordance with the invention comprises:

forming a fixed bed of solids comprising an intimately admixed composition comprising a particulate source of metal oxide support, and a particulate source of catalytically active metal oxide selected from metal oxides from groups VA, VIA, and VIIA, and passing a reactant stream containing an alcohol and oxygen through said fixed bed at conditions suitable for conversion of said alcohol to a corresponding aldehyde.

DETAILED DESCRIPTION OF THE PREFERRED EMBODIMENTS

Figure 1:
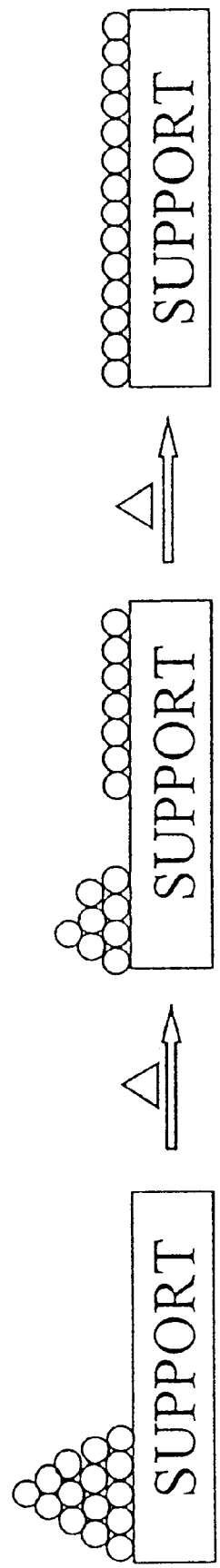
FIG. 1. A schematic of thermal spreading of a metal oxide on an oxide support surface.

In the preferred method of the present invention, mixtures of inexpensive particulate forms of a catalytically active Group VA, VIA, or VIIA metal oxide and a metal oxide support are intimately admixed and formed into a fixed catalyst bed that is subsequently used for conversion of an alcohol to its corresponding aldehyde at conventional conversion conditions. Suitable conversion conditions generally include a temperature within the range from about 150°–600 C. in a flowing stream of gas containing alcohol, oxygen, and a carrier gas that is inert to the reaction. Useful gas streams contain these reactants in a molar ratio of methanol/oxygen that is within the range of 1–4. A particularly useful stream contains 6 moles methanol to 13 moles oxygen to 81 moles of helium.

Particularly preferred catalysts according to the invention include a particulate mixture of: (a) a catalytically active metal oxide selected from Groups VA, VIA, or VIIA; and (b) a metal oxide support in the form of finely divided, intimately admixed powders that are initially loaded into a fixed catalyst bed. The preferred catalytically active metals includes an oxide or mixture of oxides of vanadium, chromium, molybdenum, tungsten, and rhenium. Preferred metal oxide supports include oxides of titanium, tin, aluminum, zirconium, cerium, niobium, tantalum, and mixtures thereof Alcohols particularly useful as feeds include virtually any of the primary, secondary, or tertiary alcohols that can be converted to aldehydes. Preferred feed alcohols to the present process include methanol, ethanol, propanol, butanol, and isomers of each.

While not wishing to be bound by theory, evidence suggests that, catalytically active metal oxide from the discrete catalytic metal oxide particles migrates during the conversion process to the support particles and forms a monolayer of catalytically active metal oxides thereon. The supported catalyst composition represents a composition having a higher specific activity than the admixed particle composition introduced into the reactor at the beginning of the conversion reaction. Such an in situ formation process represents an advance over the prior art processes relying on alkoxide impregnation methods (with its attendant costs and byproduct wastes) to form impregnated compositions of similar activity.

A preferred method for regenerating the catalyst of the present invention is via the same mechanism that contributed to its redistribution. Namely, redistribution of the catalytically active metal can be performed with an oxygen-free flow of the alcohol and inert gas through the catalyst bed at temperatures corresponding to the temperatures used for the alcohol conversion process, i.e., at a temperature within the range from about 150°–600° C. in parallel or countercurrent flow to the direction of reactant stream flow that had been used during the immediately preceding alcohol conversion process. After at least 30 minutes of such a regeneration and following a brief exposure to an alcohol-free stream containing oxygen and an inert gas, the catalyst bed can be used again for alcohol conversion to the corresponding aldehyde.

EXAMPLES

Materials $TiO_2$(P-25, ~55 $m^2$/g), $TiO_2$(anatase) and $TiO_2$(rutile) were purchased from Degussa. The $SnO_2$ support (3.7 $m^2$/g) was obtained from Aldrich. The $SiO_2$ support was fused Cab-O-Sil (Cabot, EH-5) with a BET surface area of 380 $m^2$/g. For the $TiO_2$ and fused $SiO_2$, treatment with distilled water and subsequent calcination at 550° C. were employed to improve their handling characteristics. $MoO_3$, $V_2O_5$, $CrO_3$, $Cr_2O_3$, $Re_2O_7$, $WO_3$, and $Nb_2O_5$ were purchased from Aldrich. Methanol (Alfa, Semiconductor Grade), ethanol (McCormick, Absolute-200 Proof) and 2-butanol (Aldrich, 99%) were used for alcohol oxidation. He (Linde, 99.999%) and $O_2$ (Linde, 99.99%) were procured from Linde.

Preparation of Binary Metal Oxide Physical Mixtures

Two methods were used to prepare the physical mixtures of the binary metal oxides (a) combination of an appropriate metal oxide and oxide support with pentane (Aldrich, 99+%) in a beaker, vibration for 15 minutes in an ultrasonic bath, and drying in air for 16 hrs at 100° C. and (b) grinding of a mixture of a metal oxide and an oxide support in an agate mortar for 30 min. No further thermal treatments were performed to the physical mixtures.

Alcohol Oxidation

Alcohol oxidation over loose-powder of the physical mixtures was performed in a fixed-bed reactor at atmospheric pressure and in the temperature range of 25 to 230° C. The details of the reactor system have been previously described.[13] A reactant stream of $CH_3OH$(or $C_2H_5OH$)/$O_2$/He=6/13/81 with a total flow rate of 100 ml/min was used for methanol and ethanol oxidation reactions. For 2-butanol oxidation, a gaseous mixture of 2-butanol/$O_2$/He (2.5/13/81, ml/min) was introduced into the reactor. An on-line HP 5890II GC, equipped with a Carboxene-1000 packed and a CP-sil 5 CB capillary columns for TCD and FID detectors respectively, was used to analyze the reactants and products. At the end of alcohol oxidation reactions, the used catalysts were reoxidized in $O_2$/He stream at the reaction temperatures for 30 min. In comparison, non-reaction treatments of the physical mixtures were also conducted using different gaseous streams including $O_2$/He (molar ratio=13/81), $H_2O$/$O_2$/He (molar ratio=3/13/81), and MeOH/He (molar ratio=6/81) with a total flow rate of 100 ml/min at 230° C.

Ambient and in situ Raman Studies

Raman spectra of the physical mixtures after alcohol oxidation and other treatments were recorded under hydrated or dehydrated conditions (achieved by spinning the samples or holding them stationary) in the 100–1200 $cm^{-1}$ range using a Spex triplemate spectrometer (Model 1877) equipped with a Princeton Applied Research OMA III (Model 1461) optical multichannel photodiode array detector. The 514.5 nm line of a Spectra Physics Model 171 $Ar^+$ ion laser was used for excitation. A laser power of 25 mW was typically applied to the sample. Raman measurement under dehydrated conditions was not attempted because the dehydration performed at high temperatures could possibly introduce thermal spreading for some systems.

In situ Raman spectra of the physical mixtures under methanol oxidation reaction conditions were obtained using a Spex triplemate spectrometer (Model 1877) equipped with an $Ar^+$ laser (Spectra Physics, Model 171), a Princeton Applied Research OMA III Model 1461) optical multichannel photodiode array detector, and an in situ cell.[14] A 100–200 mg self-supporting wafer was placed in the sample holder, which is mounted onto a ceramic shaft rotating at ~1500 rpm. Prior to the Raman measurement of a reference spectrum, the wafer was initially heated in an $O_2$/He (16/84, ml/min) stream at 230° C. for 30 min. A reactant mixture of $CH_3OH$/$O_2$/He (4/16/80, ml/min was subsequently introduced into the in situ cell at a flow rate of 100 ml/min and the time dependence of the in situ Raman spectra were obtained. At the end of the oxidation reaction experiment, methanol was removed from the gas stream and the catalyst was reoxidized in the $O_2$/He stream.

Example 1

Thermal Spreading of $MoO_3$ on $TiO_2$

Figure 2:
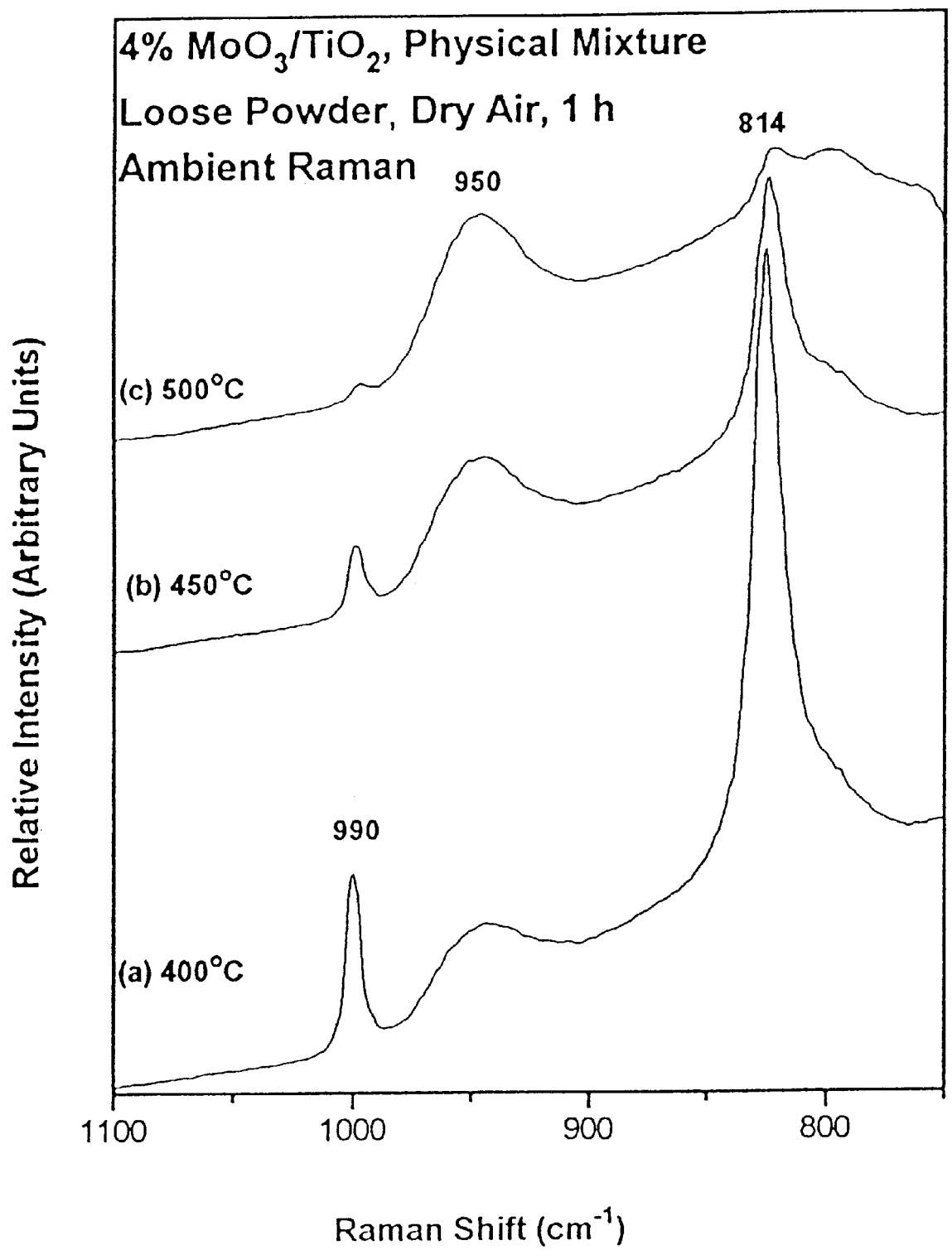
FIG. 2. Ambient Raman spectra of a 4% $MoO_3/TiO_2$ physical mixture in powder form after one-hour thermal treatment in dry air at different temperatures: (a) 400° C., (b) 450° C., and (c) 500° C.

Consistent with previous work,[7,15-19] $MoO_3$ readily spreads onto the surface of a $TiO_2$ (P25) support forming a two-dimensional surface metal oxide overlayer when their physical mixtures are thermally treated in dry air at elevated temperatures (400–500° C.). The high stability of the surface metal oxide overlayer is the consequence of the strong chemical bonding of the surface molybdena species to the $TiO_2$ surface. The ambient Raman spectra of a 4% $MoO_3$/$TiO_2$ physical mixture, in its loose powder form after a one-hour thermal treatment at temperatures of 400–500° C. in dry air, are shown in FIG. 2 in the range of 700–1100 $cm^{-1}$. Prior to the thermal treatment, only sharp Raman band at 990 and 814 $cm^{-1}$ due to crystalline $MoO_3$ were observed. After the 400° C. thermal treatment, the Raman spectra exhibit sharp 990 and 814 $cm^{-1}$ bands characteristic of crystalline $MoO_3$ and a broad band at 950 $cm^{-1}$, which was previously assigned to the vibration of a hydrated surface molybdenum oxide species.[17-19] The Raman band intensity of the surface molybdenum oxide species increases with the treatment temperature at the expense of the band intensities of crystalline $MoO_3$. After the 500° C. thermal treatment, the 990 and 814 $cm^{-1}$ Raman bands of crystalline $MoO_3$ almost disappear and the broad band at 950 $cm^{-1}$ becomes dominant.

Figure 3:
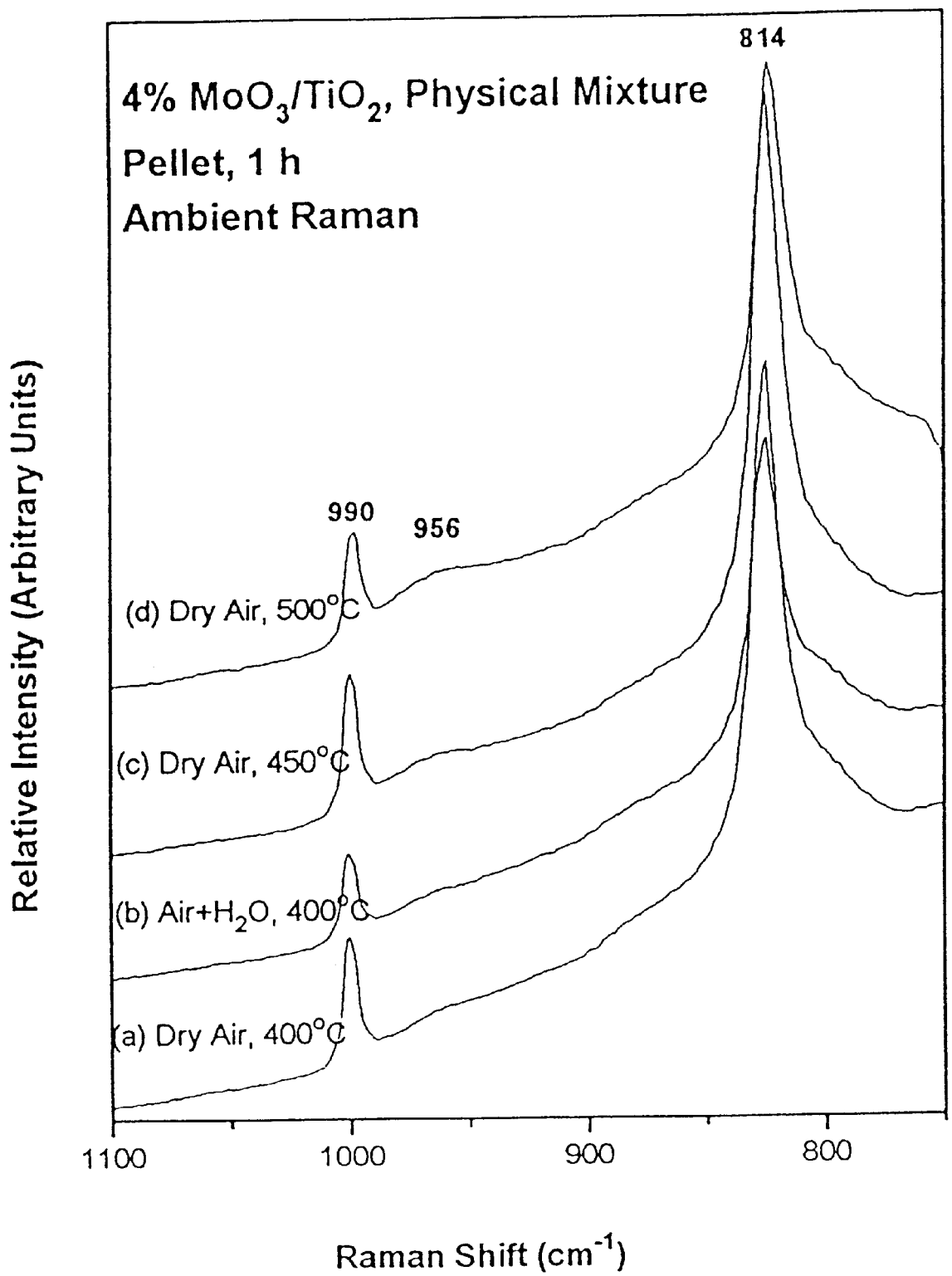
FIG. 3. Ambient Raman spectra of a 4% $MoO_3/TiO_2$ physical mixture in pellet form after one-hour thermal treatment at different conditions: (a) 400° C. and dry air, (b) 400° C. and air+$H_2O$, (c) 450° C. and dry air, and (d) 500° C. and dry air.

Similar thermal treatments were applied to the self-supporting wafers of the 4 wt % $MoO_3$/$TiO_2$ physical mixture. Interestingly, only a trace of the surface molybdenum oxide species formed after the pellets were heated at temperatures of 400–500° C. in both dry and wet air, as shown in FIG. 3. This result suggests that strong mass transfer limitations exist when the physical mixture is in the form of a self-supporting wafer.

Example 2

Thermal Spreading of $V_2O_5$ on $TiO_2$

Figure 4:
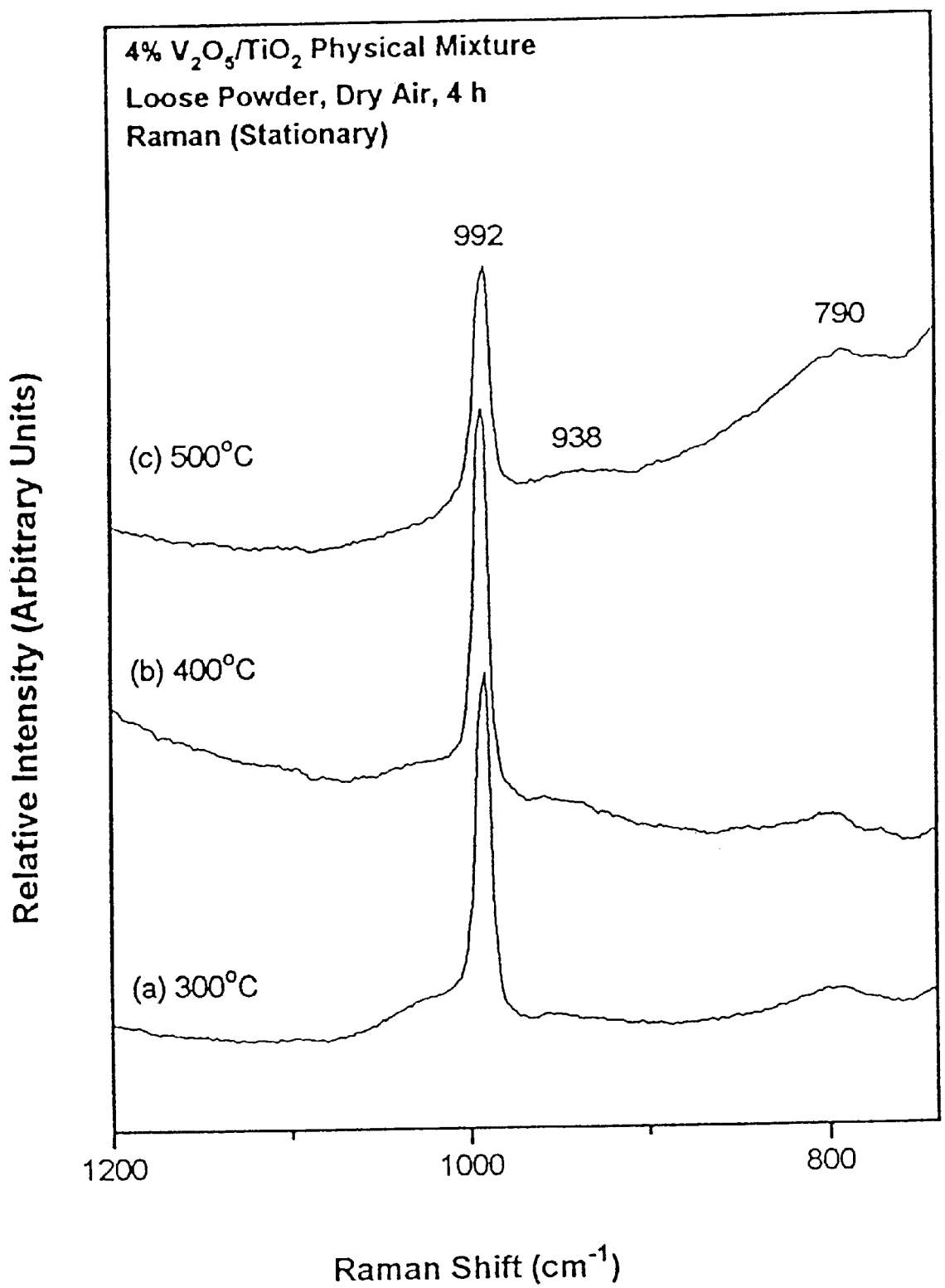
FIG. 4. Raman spectra (partially dehydrated by laser beam) of a 4% $V_2O_2/TiO_2$ physical mixture in powder form after four-hour thermal treatment in dry air at different temperatures: (a) 400° C., (b) 450° C., and (c) 500° C.
Figure 5:
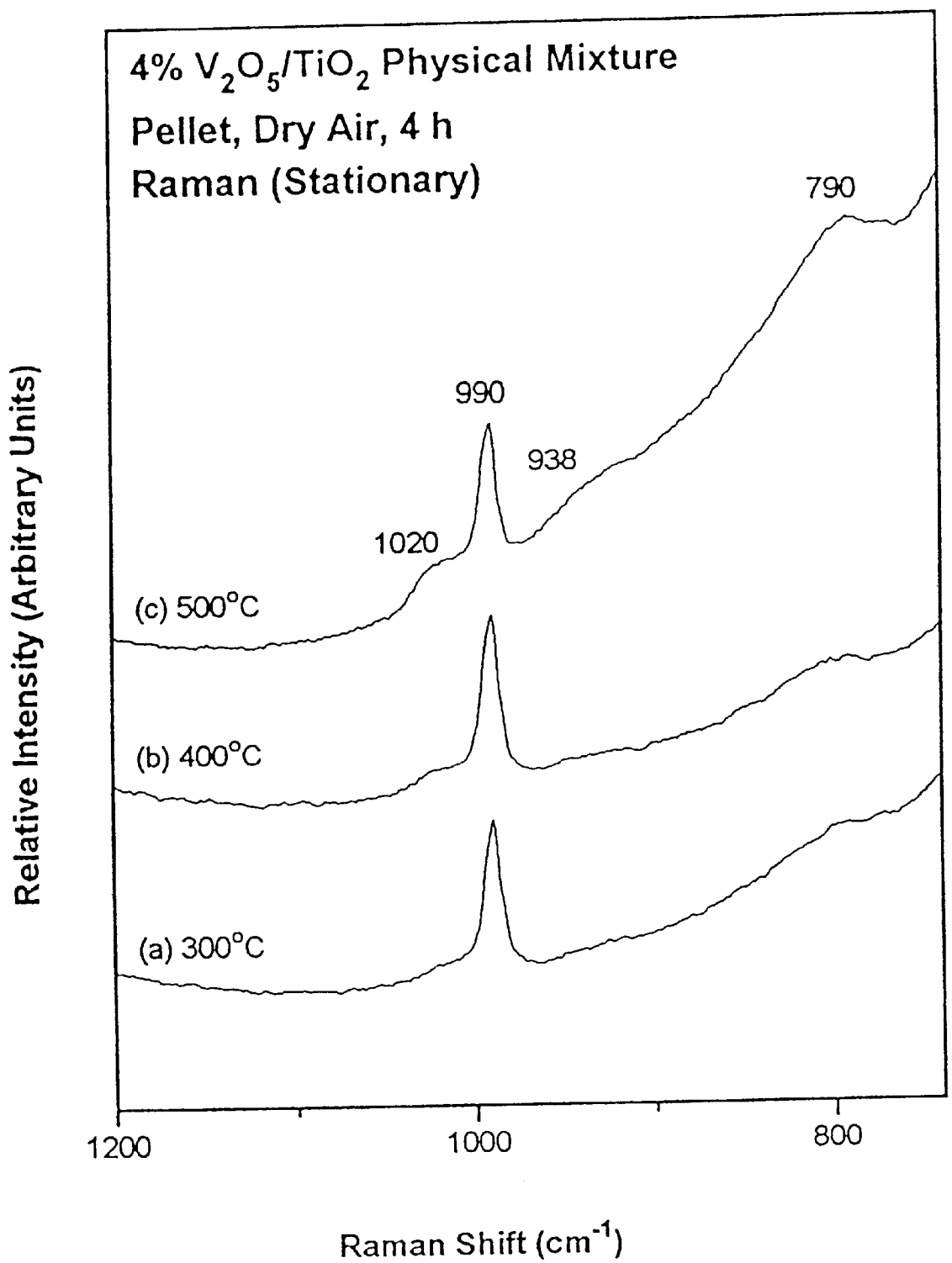
FIG. 5. Raman spectra (partially dehydrated by laser beam) of a 4% $V_2O_5/TiO_2$ physical mixture in pellet form after four-hour thermal treatment in dry air at different conditions: (a) 300° C., (b) 400° C., (c) 500° C.

The Raman spectra of a 4 wt % $V_2O_5$/$TiO_2$ physical mixture in both loose powder and pellet catalyst forms, after four-hour 300–500° C. treatments in dry air, are present in FIGS. 4 and 5, respectively. The Raman spectra were obtained by holding the samples stationary to achieve dehydration of the surface vanadium oxide species by the laser beam so that the surface vanadium oxide species can be discriminated from bulk $V_2O_5$. The sharp 990 cm$^{-1}$ Raman band is characteristic of crystalline $V_2O_5$, and the ~790 cm$^{-1}$ band is due to the first overtone of the 395 cm$_{-1}$ band of the $TiO_2$ anatase support. The absence of the broad features at ~1022 and 938 cm$^{-1}$ due to the surface vanadium oxide species reveals that thermal spreading of $V_2O_5$ on $TiO_2$ almost did not occur when their physical mixture powder samples were treated in dry air at 300 and 400° C. for 4 h. Very weak Raman bands at ~1022 and/or 938 cm$^{-1}$ developed only when the physical mixture samples were treated at 500° C. (see FIGS. 4c and 5c), indicating that a small amount of crystalline $V_2O_5$ had thermally spread onto the $TiO_2$ support surface. The ~1022 cm$^{-1}$ Raman band has been assigned to the V=O vibration of distorted surface $VO_4$ species present under dehydrated conditions and the ~938 cm$^{-1}$ Raman band is associated with a two-dimensional polymerized $VO_4$ species.[19]

The thermal spreading of $V_2O_5$ on $TiO_2$ reported in the literature is somewhat conflicting regarding the treatment conditions under which the surface vanadium oxide species forms.[18-22] The discrepancies relate to the preparation methods of the physical mixtures, and surface area and impurities.[23,39]

Example 3

Reaction Induced Spreading of $MoO_3$ on $TiO_2$

Figure 6:
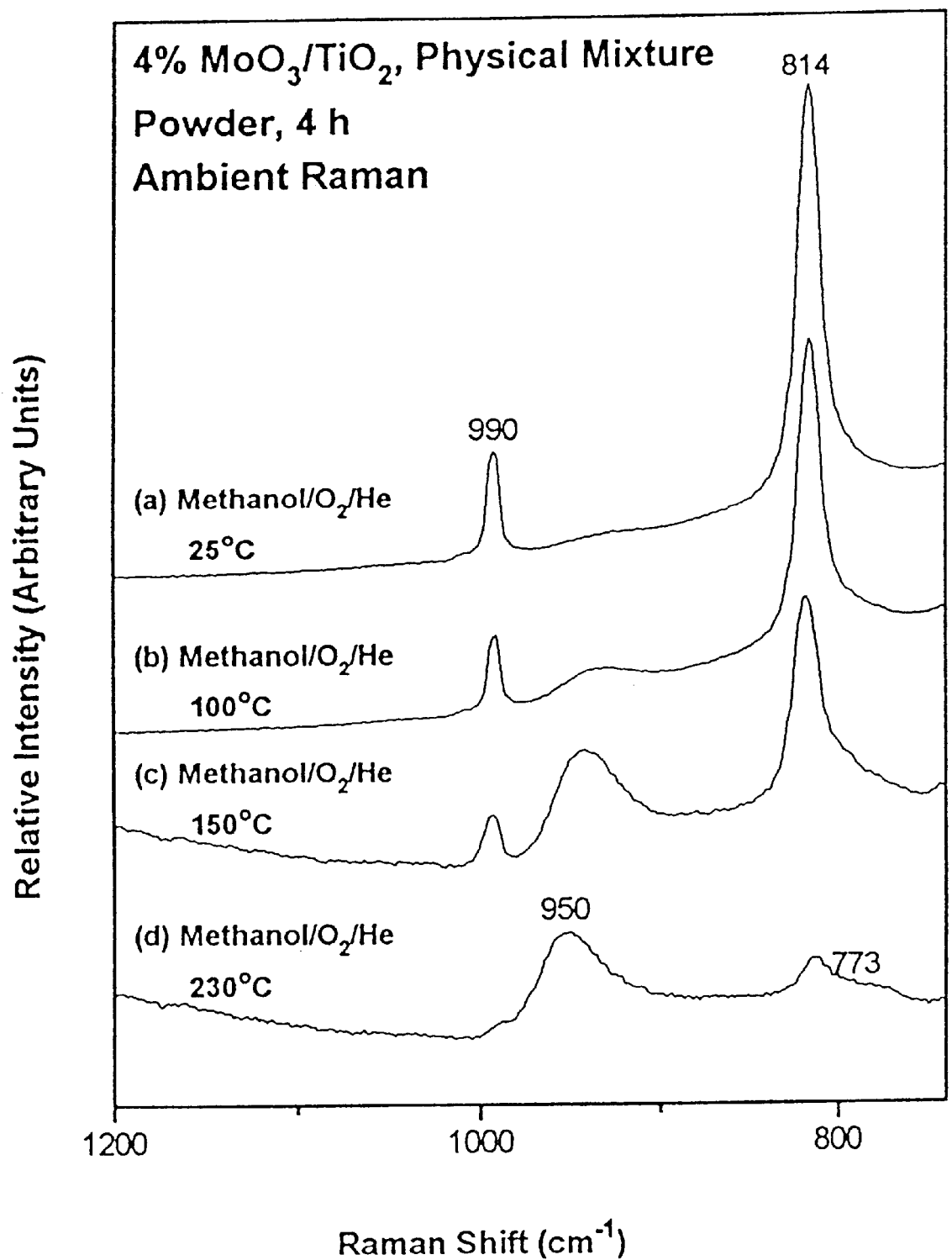
FIG. 6. Ambient Raman spectra of a 4% $MoO_3/TiO_2$ physical mixture in powder form after four hours of methanol oxidation at different reaction temperatures: (a) 25° C., (b) 100° C., (c) 150° C., and (d) 230° C.

The ambient Raman spectra of the 4 wt % $MoO_3/TiO_2$ physical mixture samples after four hours of methanol oxidation at 25 to 230° C. are shown in FIG. 6.). After methanol oxidation at 25° C. for 4 h, the Raman spectrum was essentially identical to that of crystalline $MoO_3$ (FIG. 6a). Even at 100° C., however, methanol oxidation leads to the formation of a considerable amount of surface molybdenum oxide species on $TiO_2$, evidenced by the presence of the broad Raman band at 950 cm$^{-1}$ shown in FIG. 6b. Variation of the reaction temperatures from 100 to 230° C. leads to the dominance of the surface molybdenum oxide species only with a trace of crystalline $MoO_3$ present in the final mixture catalyst (see FIG. 6d). The spreading of $MoO_3$ onto the $TiO_2$ support during methanol oxidation reactions occurred at very mild temperatures that are much lower than the Tammann temperature (261° C.) of crystalline $MoO_3$.

Figure 7:
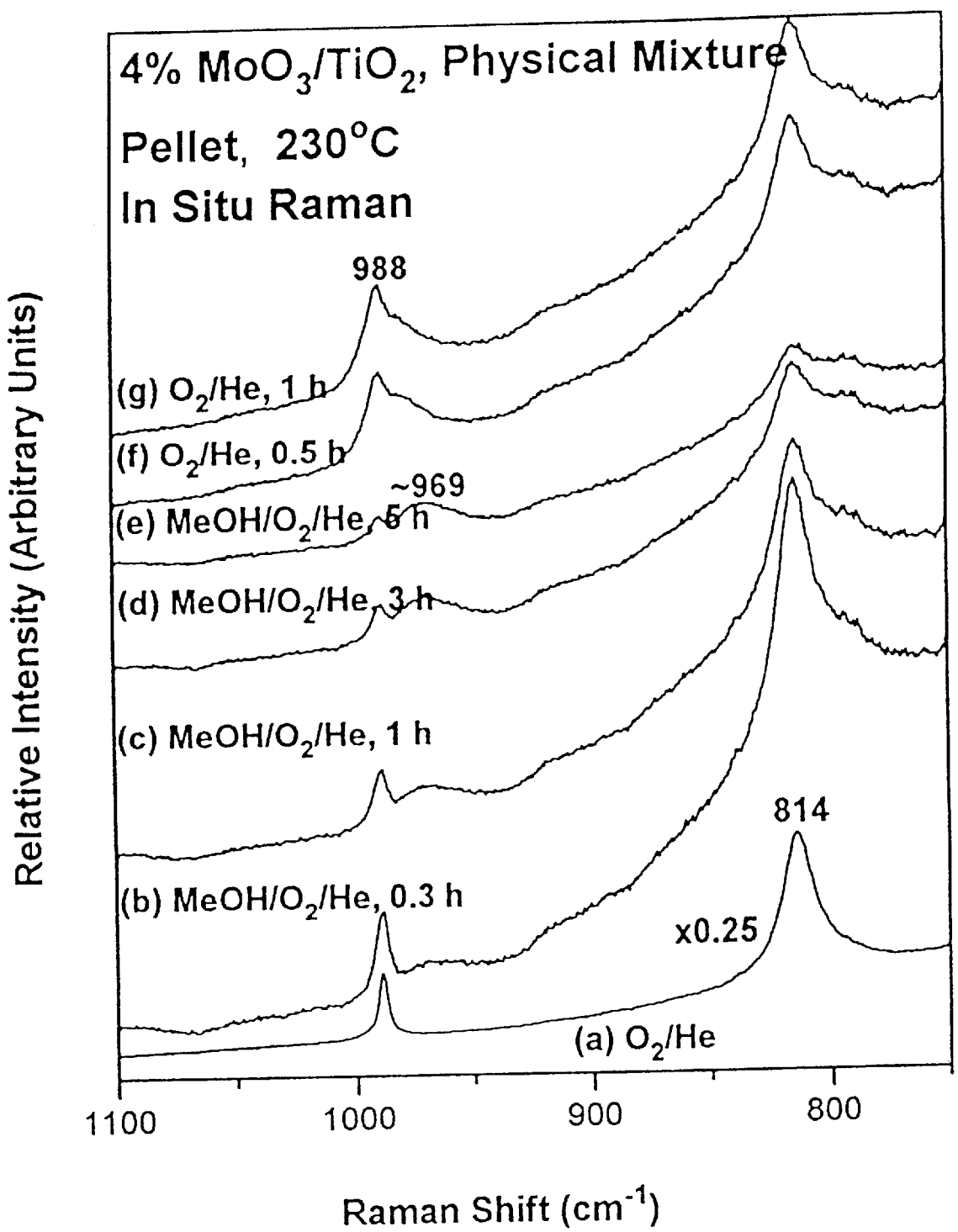
FIG. 7. In situ Raman spectra of a 4% $MoO_3/TiO_2$ physical mixture in pellet form during methanol oxidation at 230° C.: (a) before methanol oxidation, (b) 20 min, (c) 1 h, (d) 3 h, (e) 5 h, (f) after oxidation for 0.5 h, and (g) after oxidation for 1 h.

Direct evidence for reaction-induced spreading also comes from the in situ Raman studies during methanol oxidation as shown in FIG. 7 over a catalyst pellet consisting of a 4% $MoO_3/TiO_2$ physical mixture at 230° C. Prior to methanol oxidation, the Raman spectrum (FIG. 7a) only possesses the strong Raman bands of crystalline $MoO_3$ at 814 and 988 cm$^{-1}$. Upon exposure to the methanol oxidation reaction conditions, the sharp Raman bands due to crystalline $MoO_3$ slowly diminish with reaction time and a new broad Raman band at 969 cm$^{-1}$ is formed (FIGS. 7b–e). The in situ Raman band at 969 cm$^{-1}$ has previously been assigned to a surface molybdenum oxide coordinated to methoxy species.[24] Upon switching to an $O_2$/He stream, the Raman band at 969 cm$^{-1}$ shifted to about 990 cm$^{-1}$ due to the decomposition of the surface molybdate methoxy complex to a dehydrated surface molybdenum oxide species (FIGS. 7f and g). Simultaneously, there was also an increase in the crystalline $MoO_3$ 814 and 988 cm$^{-1}$ Raman bands due to the oxidation of the partially reduced $MoO_3$ particles during the methanol oxidation reaction. Further increasing the reaction temperature to 300° C. for about an hour resulted in the complete disappearance of the crystalline $MoO_3$ Raman bands and only the appearance of the Raman bands associated with the surface molybdenum oxide species (not shown here). Reoxidation of the sample at 300° C. again resulted in the appearance of weak crystalline $MoO_3$ Raman bands revealing that some residual reduced crystallites still remained and that higher temperature treatments or reaction times are required for the complete spreading of $MoO_3$ on the titania support.

Figure 8B:
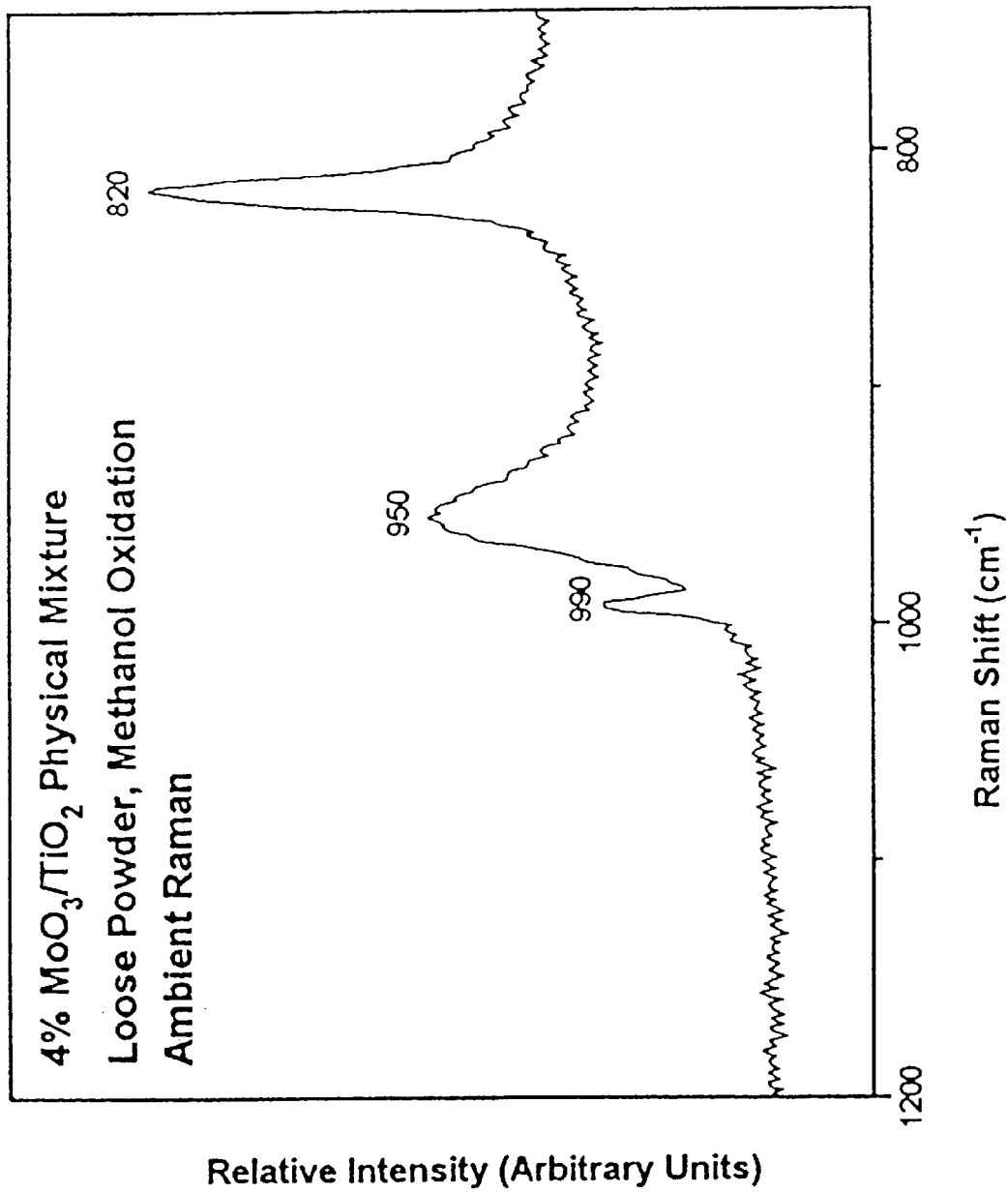
FIG. 8. (A) Plot of TOF and formaldehyde selectivity versus reaction time over a 4% $MoO_3/TiO_2$ physical mixture catalyst in powder form in comparison with the TOF (solid line) and formaldehyde selectivity (dot line) of a 4% $MoO_3/TiO_2$ supported catalyst prepared by impregnation; (B) Ambient Raman spectrum of the 4% $MoO_3/TiO_2$ physical mixture catalyst after methanol oxidation.

The reaction-induced spreading of $MoO_3$ on $TiO_2$ is also reflected by the variation of the catalytic properties of the physical mixture catalysts with reaction time during methanol oxidation. The dependence of the methanol oxidation activity and formaldehyde selectivity on reaction time was studied over 60 mg of a 4% $MoO_3/TiO_2$ physical mixture catalyst at 230° C. and is shown in FIG. 8(A). The methanol oxidation activity has been normalized to the number of methanol molecules converted per total molybdenum atoms per second (i.e., the turnover frequency—TOF) even though the dispersion of the Mo component is changing with reaction time until complete spreading of crystalline $MoO_3$. The catalytic activity of the physical mixture increases with reaction time from an initial TOF of 0.02 s$^{-1}$ at 5 min to a TOF of 0.038 s$^{-1}$ at 455 min and finally approaches the catalytic activity (TOF=0.045 s$^{-1}$) of a 4% $MoO_3/TiO_2$ catalyst prepared by alkoxide impregnation. The selectivity to formaldehyde also increases over the first period of 70 min and approaches the formaldehyde selectivity (73%) of the 4% $MoO_3/TiO_2$ catalyst prepared by impregnation.

Previous investigations have revealed that the surface molybdenum oxide species is the active site for methanol oxidation to formaldehyde.[24] The simultaneous increase in both catalytic activity and formaldehyde selectivity of the 4% $MoO_3/TiO_2$ physical mixture catalyst with reaction time directly corresponds to the gradual spreading of $MoO_3$ onto the $TiO_2$ support surface. The corresponding Raman spectrum of the 4% $MoO_3/TiO_2$ physical mixture after methanol (shown in FIG. 8(B)) confirms that almost complete transformation of crystalline $MoO_3$ into surface molybdenum oxide species has occurred.

Figure 9:
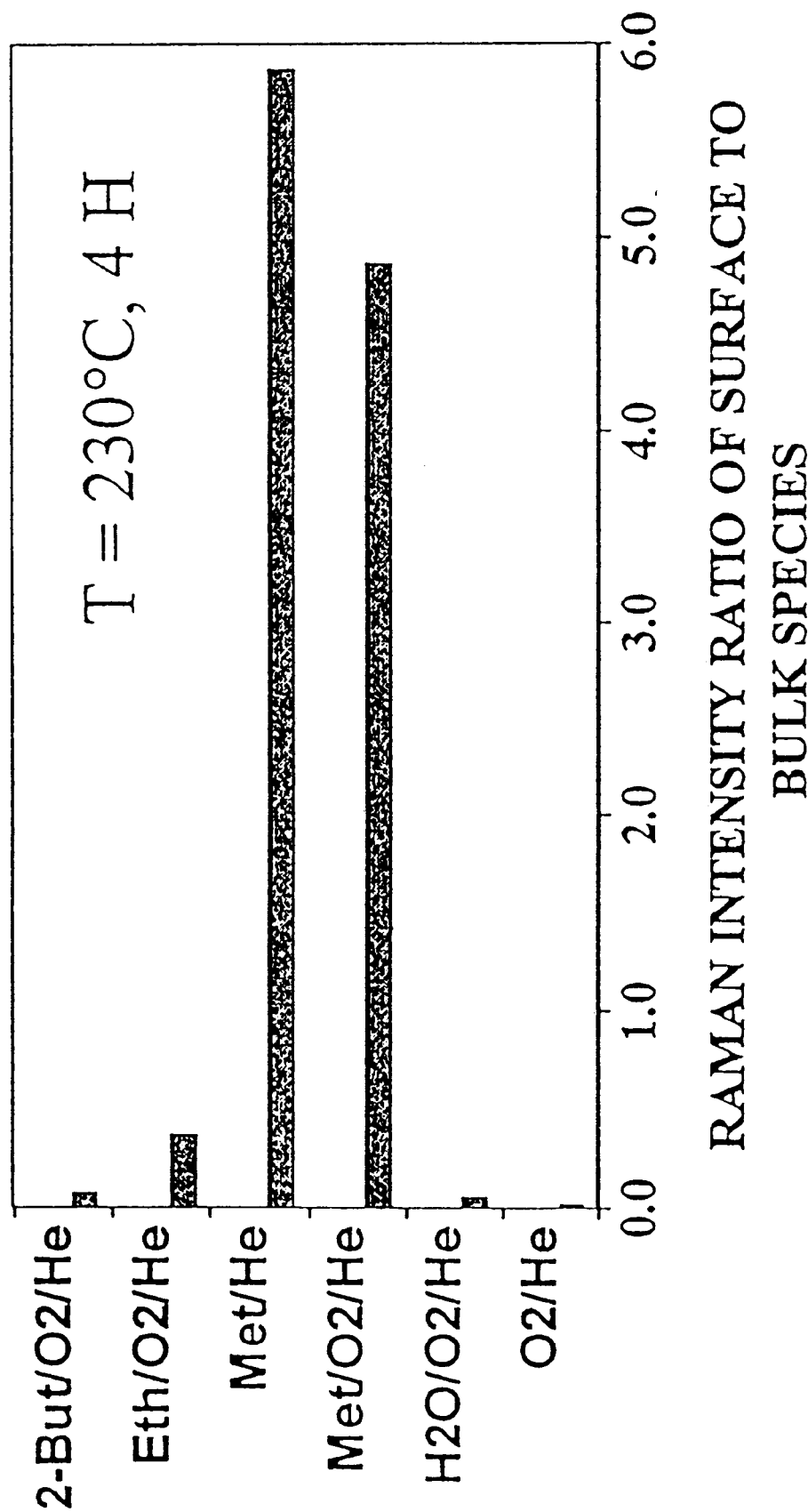
FIG. 9. Dependence of Raman band intensity ratios ($I_{950}/I_{990}$) of surface molybdate to crystalline $MoO_3$ in a 4 wt % $MoO_3/TiO_2$ physical mixture on alcohol oxidation and other gaseous stream treatment conditions at 230° C. for 4 h.

The studies were further extended to examine the effects of higher alcohol oxidation (ethanol and 2-butanol) on reaction-induced spreading of $MoO_3$ on $TiO_2$. The dependence of Raman band intensity ratios ($I_{950}/I_{990}$) of surface molybdenum oxide species to crystalline $MoO_3$ in the 4% $MoO_3/TiO_2$ physical mixture samples on different alcohol oxidation reactions (methanol, ethanol, and 2-butanol) at 230° C. for 4 h are represented in FIG. 9. For comparison, the dependence of Raman band intensity ratios ($I_{950}/I_{990}$) on different treatments of $O_2$/He, $H_2O/O_2$/He, and methanol/He gas streams at 230° C. for 4 h are also present in FIG. 9. These results demonstrate that the spreading of $MoO_3$ on $TiO_2$ follows the trend: methanol>>ethanol>2-butanol, water>oxygen. Furthermore, an oxygen-free methanol environment is also highly favorable to the transformation of crystalline $MoO_3$ into the surface molybdenum oxide species, suggesting that methanol is the key component that is associated with the $MoO_3$ spreading onto the $TiO_2$ support surface during methanol oxidation.

Figure 10:
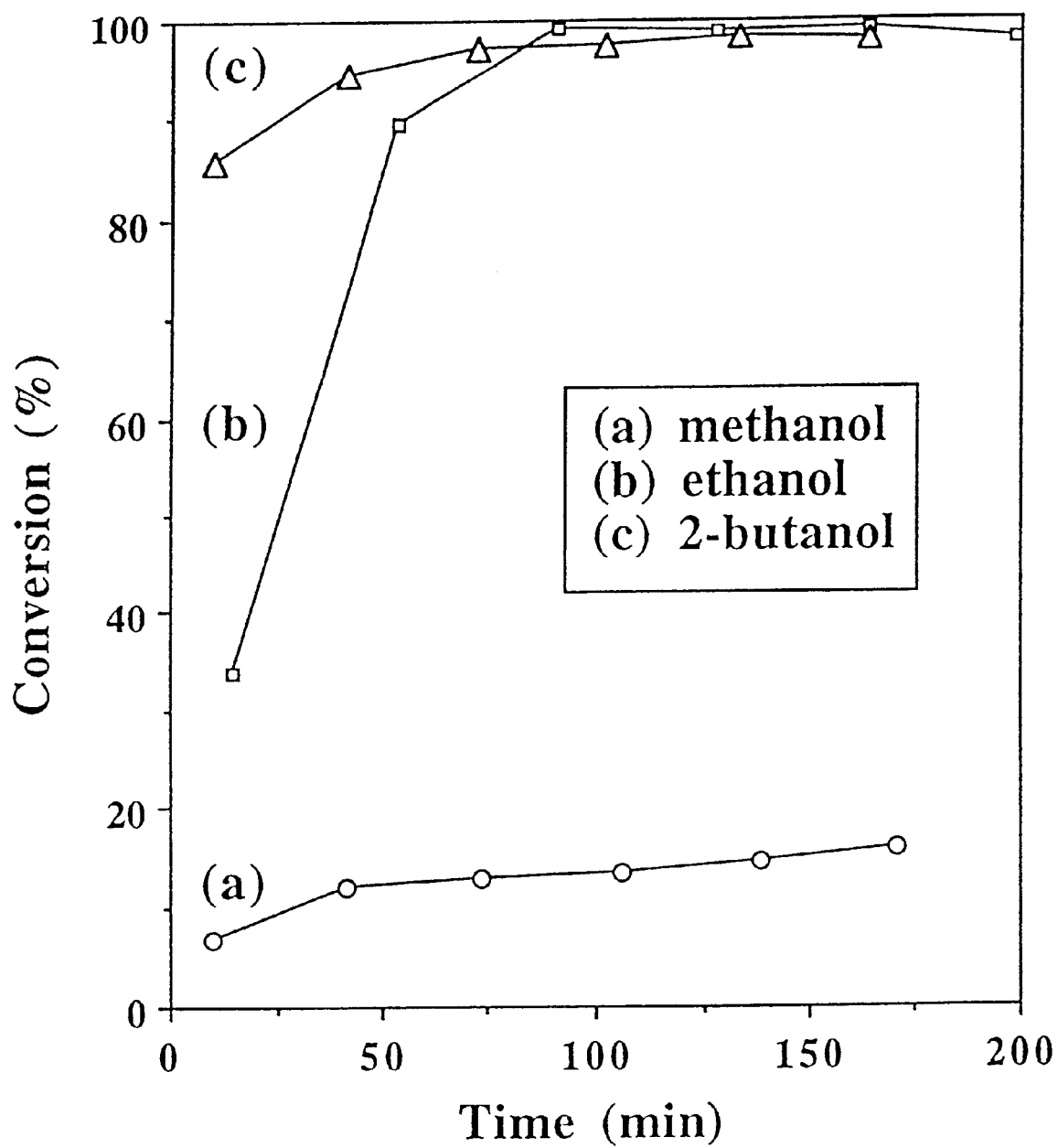
FIG. 10. Alcohol conversions over a 4% $MoO_3/TiO_2$ physical mixture in powder form at 230° C. as a function of reaction time: (a) methanol oxidation, (b) ethanol oxidation, and (c) 2-butanol oxidation.

The reaction-induced spreading of $MoO_3$ on $TiO_2$ is also reflected in the continuous increase of alcohol conversion (methanol, ethanol, and 2-butanol) with reaction time, as shown in FIG. 10. The methanol conversion over the 4% $MoO_3/TiO_2$ physical mixture continuously increased from about 8 to 16% during the first three hours of reaction. The higher alcohols were more active than methanol due to their weak a-C—H bonds and their conversions also increased continuously with reaction time. Thus, the increase in alcohol conversion as a function of time over the $MoO_3/TiO_2$ physical mixture catalysts is directly related to the transformation of crystalline $MoO_3$ into the surface molybdenum oxide species in the $TiO_2$ support.

Example 4

Reaction Induced Spreading to $MoO_3$ on $SnO_2$

Figure 11:
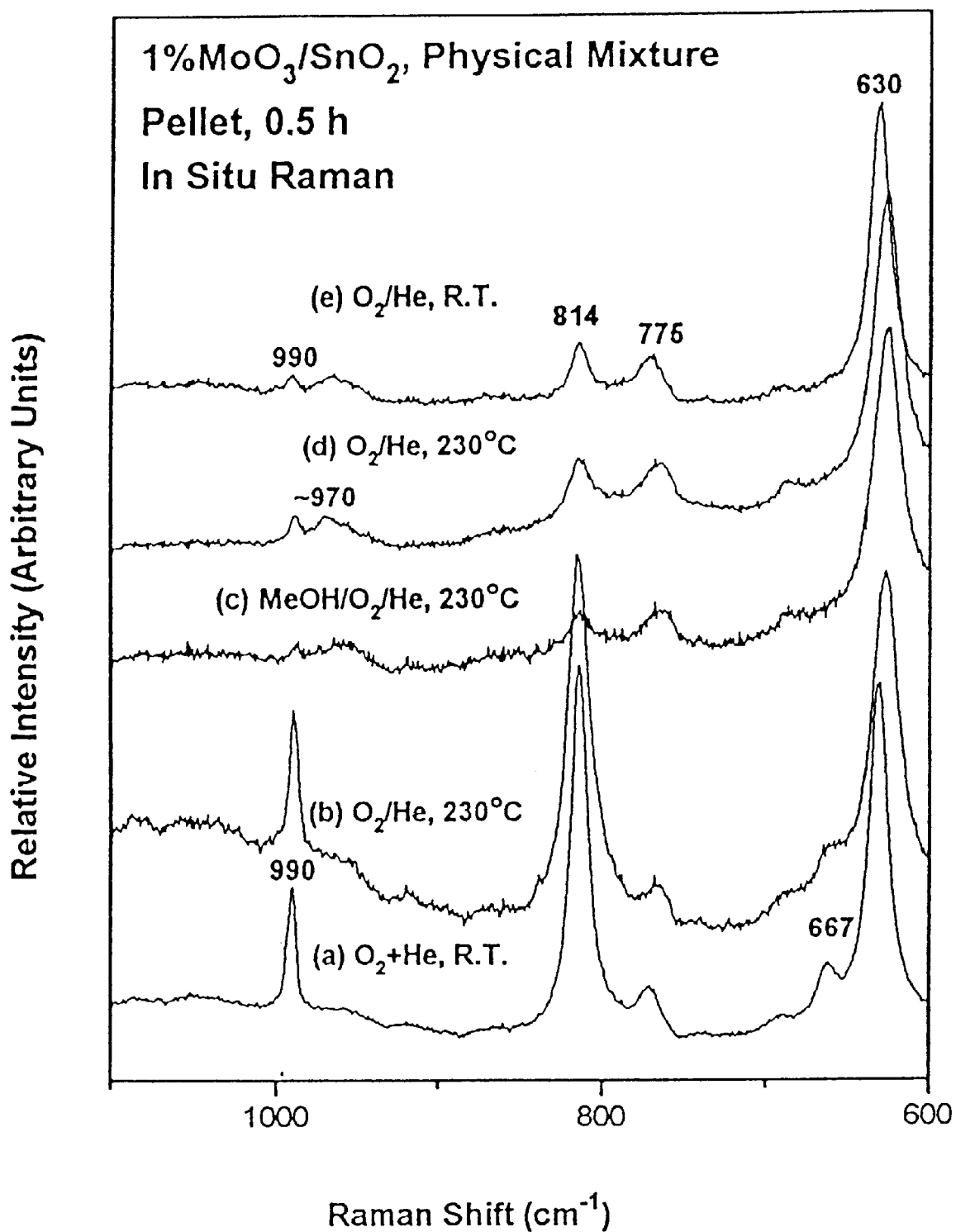
FIG. 11. In situ Raman spectra of a 1% $MoO_3/SnO_2$ physical mixture in pellet form during methanol oxidation: (a) before methanol oxidation, room temperature; (b) before methanol oxidation, 230° C., 30 min; (c) methanol oxidation, 230° C., 30 min; (d) after oxidation, 230° C., 30 min; and (e) after oxidation, room temperature.

The reaction-induced spreading of $MoO_3$ also readily occurs on different oxide supports during methanol oxidation at mild temperatures. The in situ Raman spectra of a 1 wt % $MoO_3/SnO_2$ physical mixture acquired during methanol oxidation and treatments in an $O_2/He$ stream at 230° C. are shown in FIG. 11. The Raman features at 630 and 775 $cm^{-1}$ are due to the $SnO_2$ support.[25] The sharp 990, 814, 667 $cm^{-1}$ Raman bands, characteristic of crystalline $MoO_3$, nearly disappeared after half-hour methanol oxidation at 230° C. and a broad band at ~970 $cm^{-1}$ due to a surface molybdenum oxide methoxy species[24] is observed (FIG. 11c). Subsequent reoxidation with $O_2/He$ at 230° C. slightly increases the band intensities of both the surface molybdenum oxide species and crystalline $MoO_3$ (FIG. 11d).

Example 5

Reaction Induced Spreading of $MoO_3$ on $SiO_2$

Figure 12A:
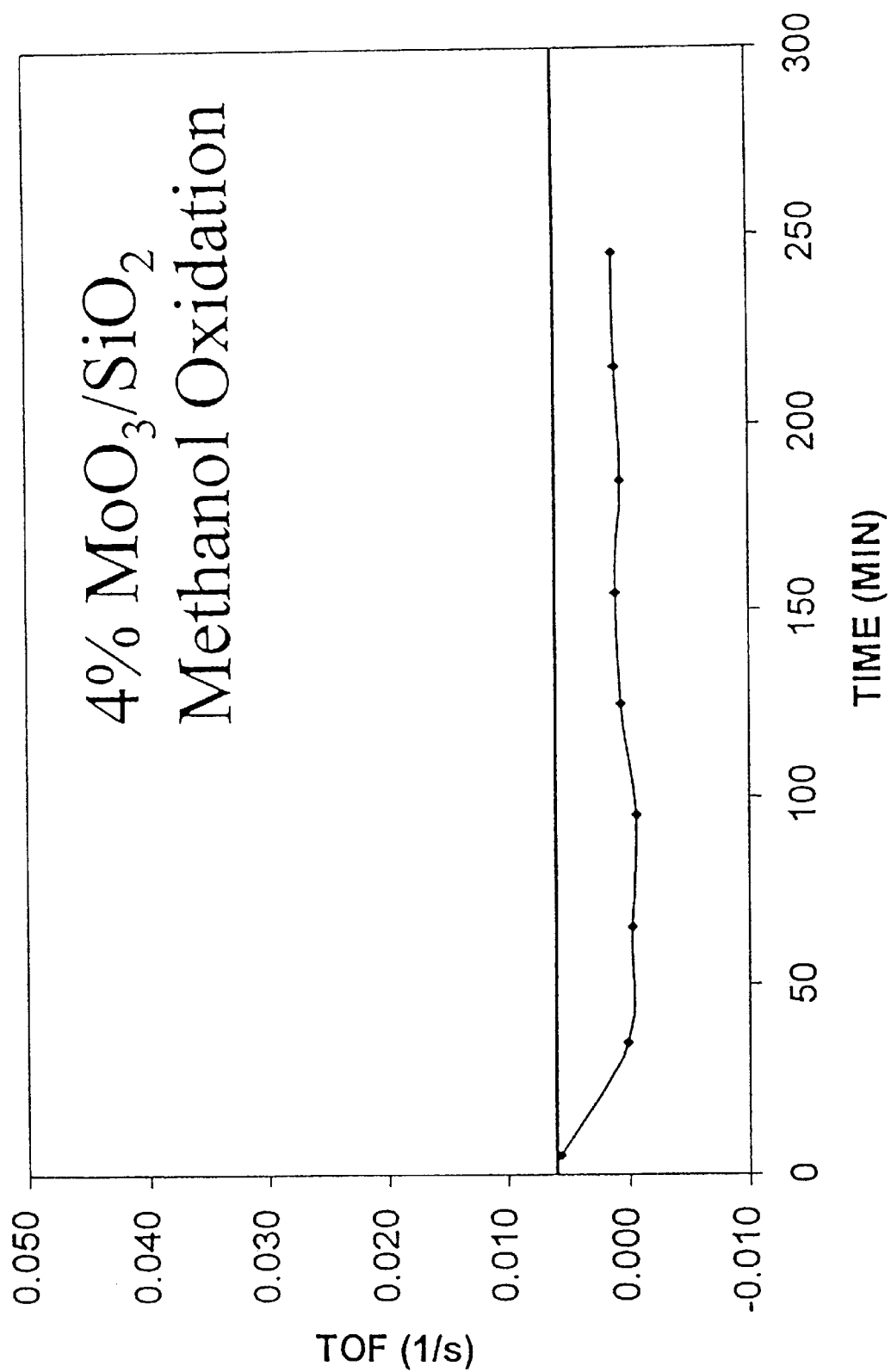
FIG. 12. (A) Plot of TOF versus the reaction time over a 4% $MoO_3/SiO_2$ physical mixture catalyst in powder form in comparison with the initial TOF of a 4% $MoO_3/SiO_2$ supported catalyst prepared by impregnation; (B) Ambient Raman spectra of the 4% $MoO_3/SiO_2$ physical mixture catalyst before methanol oxidation (a) and after methanol oxidation (b).

In the case of silica support, it is expected that no spreading of $MoO_3$ should be observed during methanol oxidation since the surface molybdenum oxide species are not stable and transformed to crystalline b-$MoO_3$ under methanol oxidation conditions.[26] The methanol oxidation TOFs of a 4 wt % $MoO_3/SiO_2$ physical mixture as a function of reaction time at 230° C. are shown in FIG. 12(A). In contrast to the results for the 4 wt % $MoO_3/TiO_2$ physical mixture, the methanol oxidation activity of the 4 wt % $MoO_3/SiO_2$ physical mixture does not increase with reaction time and has no tendency to approach the initial TOF (0.07 $s^{-1}$) of a 4 wt % $MoO_3/SiO_2$ catalyst, which was prepared by alkoxide impregnation.

The formaldehyde selectivity data were not obtained due to low methanol conversion. Thus, the results demonstrate that crystalline $MoO_3$ does not spread onto the $SiO_2$ support during methanol oxidation reactions.

Figure 12B:
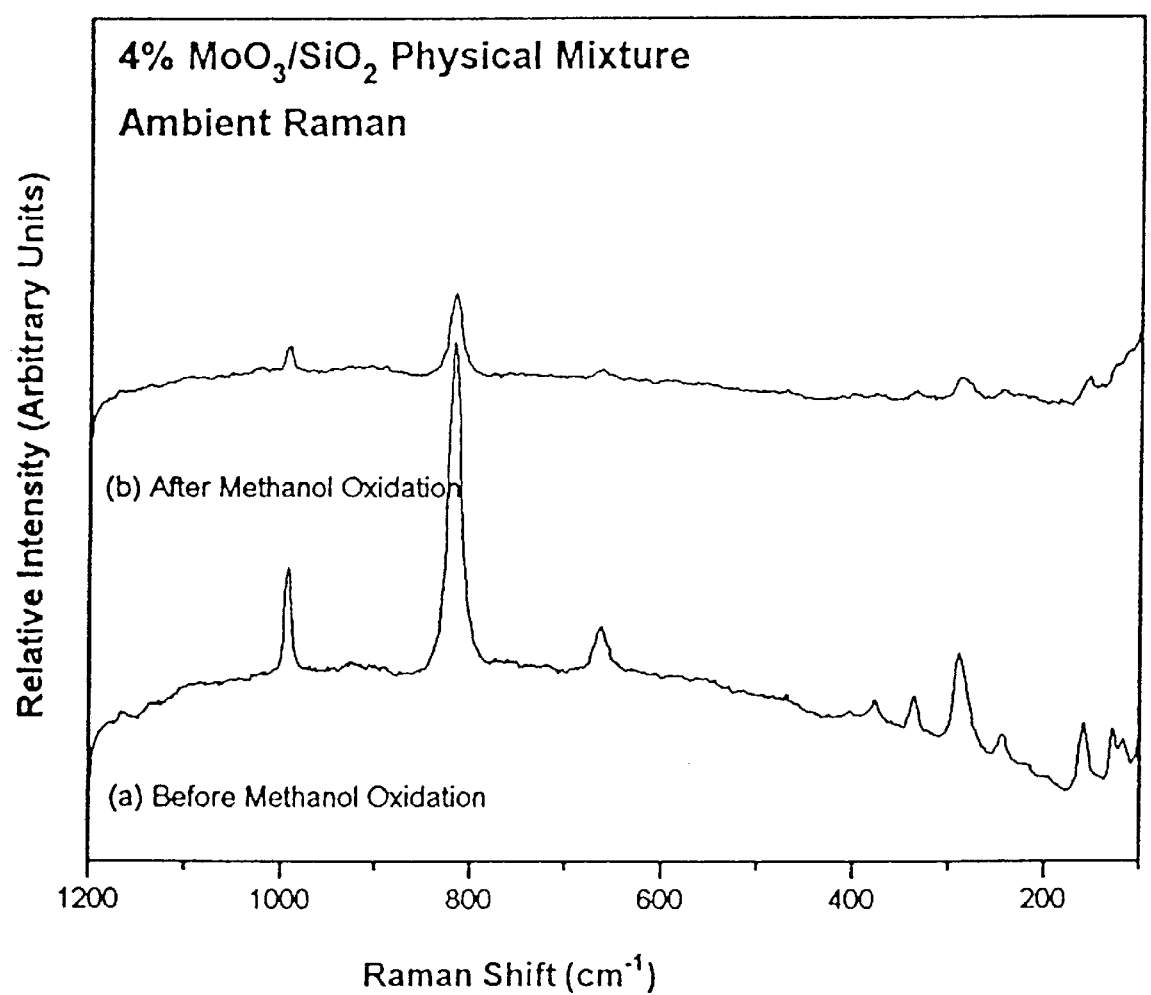

The corresponding Raman spectra of the 4 wt % $MoO_3/SiO_2$ physical mixture catalyst before and after methanol oxidation (presented in FIG. 12(B)) show that only the Raman bands due to crystalline $MoO_3$ are observed and that the Raman bands of crystalline $MoO_3$ after methanol oxidation are much weaker than those before methanol oxidation, suggesting that a significant amount of crystalline $MoO_3$ was taken away from the 4 wt % $MoO_3/SiO_2$ physical mixture catalyst. This is further evidenced by the observation that a large amount of crystalline $MoO_3$ was found to deposit at the cooler exit of the reactor and that the color of the 4 wt % $MoO_3/SiO_2$ physical mixture catalyst after methanol oxidation was close to that of pure $SiO_2$.

Example 6

Reaction Induced Spreading of $V_2O_5$ on $TiO_2$

Figure 13:
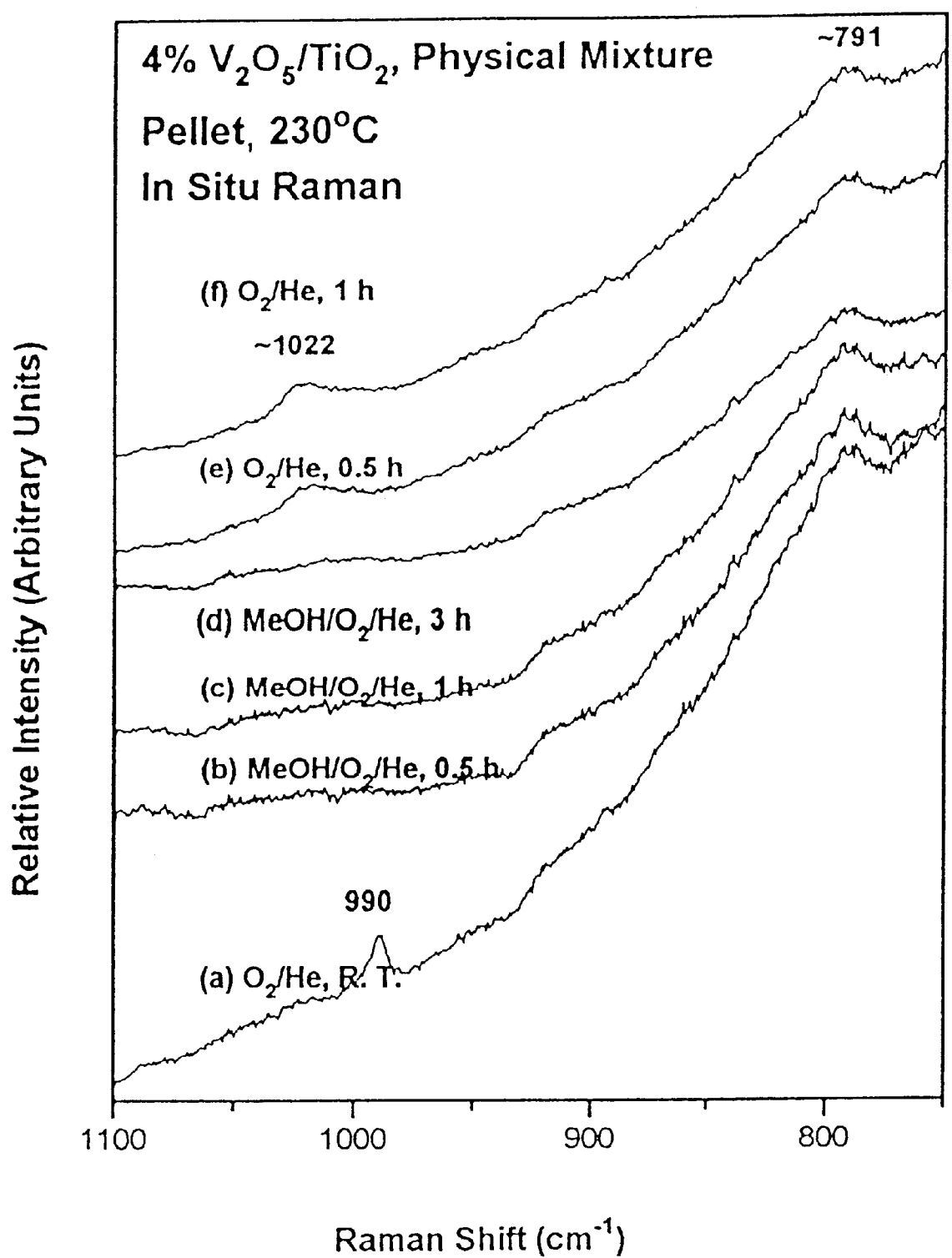
FIG. 13. In situ Raman spectra of a 4% $V_2O_5/TiO_2$ physical mixture in pellet form during methanol oxidation at 230° C.: (a) before methanol oxidation, room temperature; (b) methanol oxidation, 0.5 h; (c) methanol oxidation, 1 h; (d) methanol oxidation, 3 h; and (e) after oxidation, 0.5 h; and (f) after oxidation, 1 h.

The in situ Raman spectra of a self-supported wafer consisting of a 4% $V_2O_5/TiO_2$ physical mixture are shown during methanol oxidation at 230° C. in FIG. 13. The starting sample only exhibits the Raman bands of crystalline $V_2O_5$ at about 990 $cm^{-1}$ and the titania support at about 790 $cm^{-1}$ (FIG. 13a). Exposure of the 4% $V_2O_5/TiO_2$ catalyst to the methanol oxidation reaction at 230° C. completely removes the Raman bands of the $V_2O_5$ crystals and no new bands due to surface vanadia species are observed (FIGS. 13b–d). The complete absence of any vanadia Raman bands suggests that the vanadia component of the catalyst was reduced (reduced vanadia gives rise to very weak Raman bands)[27] Reoxidation of the 4% $V_2O_5/TiO_2$ physical mixture catalyst wafer resulted in the appearance of a new Raman band at 1022 $cm^{-1}$ associated with surface vanadia species (FIGS. 13e–f)[14,19,28] and the complete absence of crystalline $V_2O_5$ particles. Thus, the in situ Raman studies demonstrate that crystalline $V_2O_5$ completely transformed into the surface vanadium oxide species during methanol oxidation at a very mild temperature, 230° C.

Figure 14A:
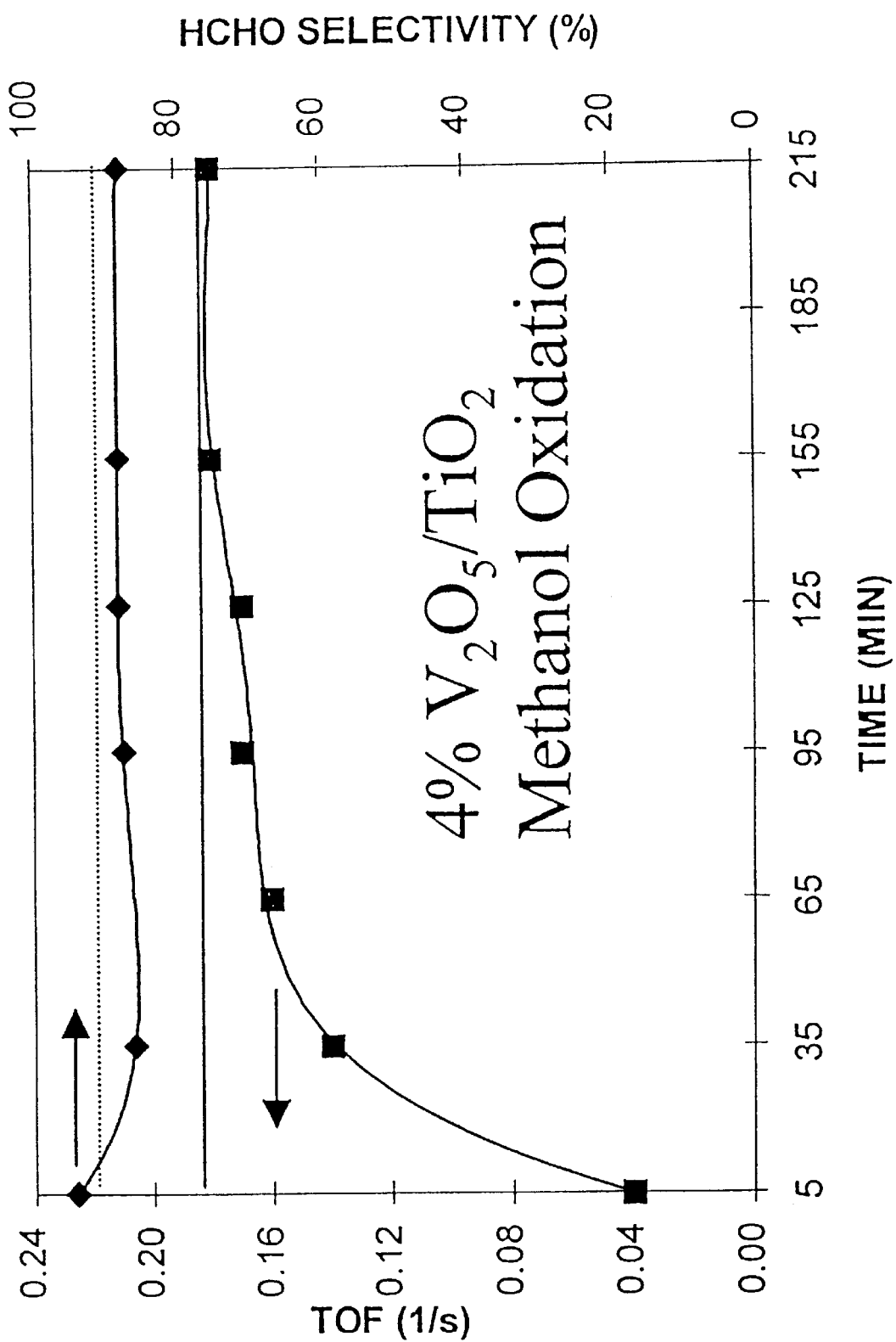
FIG. 14. (A) Plot of TOF and formaldehyde selectivity versus the reaction time over a 4% $V_2O_3/TiO_2$ physical mixture catalyst in powder form in comparison with the TOF (solid line) and formaldehyde selectivity (dot line) of a 4% $V_2O_3/TiO_2$ supported catalyst prepared by impregnation; (B) Raman spectrum (partially dehydrated by laser beam) of the 4% $V_2O_3/TiO_2$ physical mixture catalyst after methanol oxidation.

The structural changes in the $V_2O_5/TiO_2$ physical mixture catalyst result in changes in the methanol oxidation activity and selectivity pattern of this catalyst. A detailed example of the evolution of the activity and formaldehyde selectivity with reaction time is observed during methanol oxidation in a fixed bed reactor with 10 mg of the 4% $V_2O_5/TiO_2$ physical mixture at 230° C, shown in FIG. 14(A). The catalytic activity of the $V_2O_5/TiO_2$ physical mixture catalyst continuously increases with reaction time during the initial period of methanol oxidation. When the reaction time exceeded 3 h, corresponding to the time required for complete spreading of $V_2O_5$ on $TiO_2$ to occur, a constant activity is observed, which is the same as that (TOF=0.185 $s^{-1}$) of a 4% $V_2O_5/TiO_2$ catalyst prepared by alkoxide impregnation. The formaldehyde selectivity remained essentially constant at all the conversion levels. These results are consistent with the previous conclusion that the surface vanadium oxide species is the active site for methanol oxidation.[13]

Figure 14B:
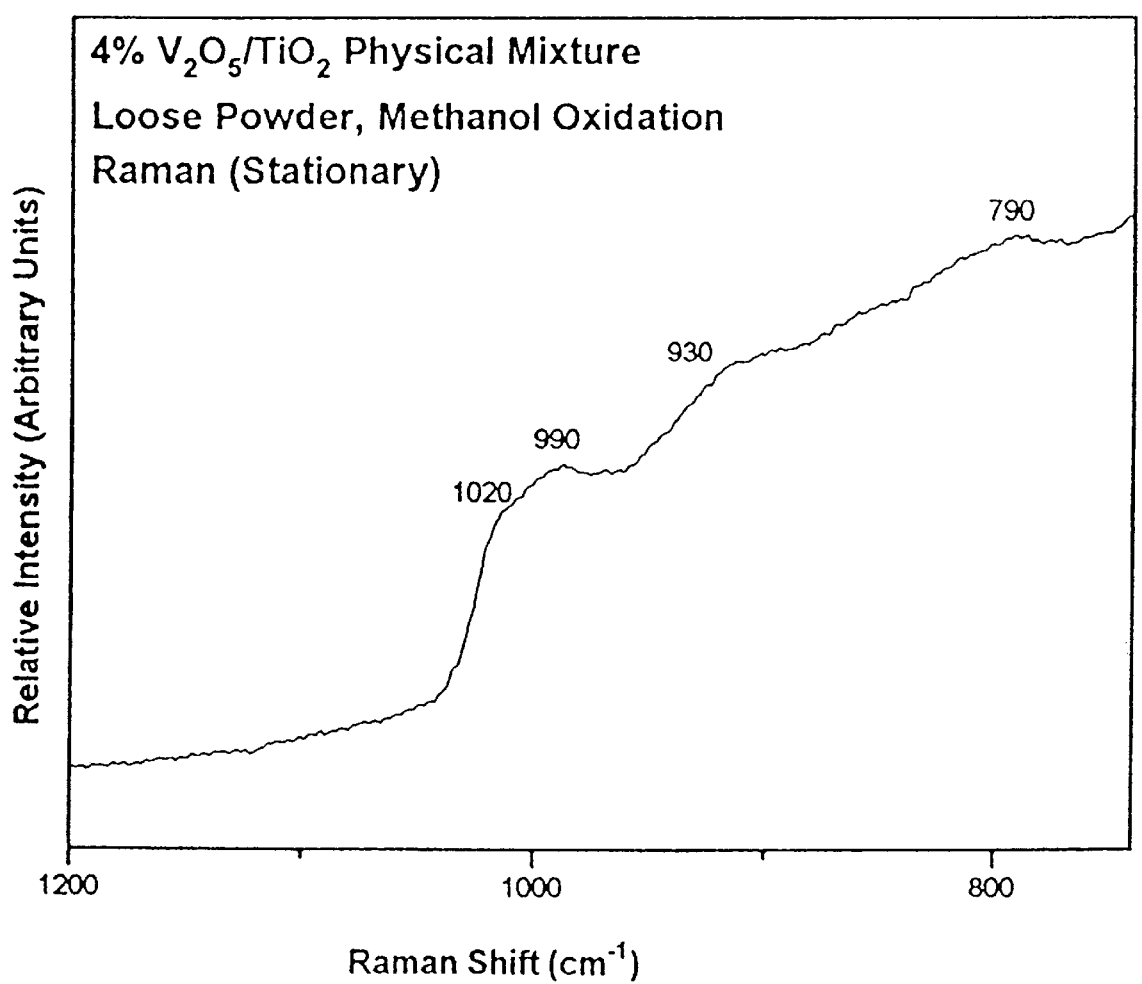

The corresponding Raman spectrum of the 4% $V_2O_5/TiO_2$ physical mixture after methanol oxidation reveals that complete spreading of crystalline $V_2O_5$ onto the $TiO_2$ surface as two-dimensional vanadium oxide species occurred, as shown in FIG. 14(B).

Figure 15:
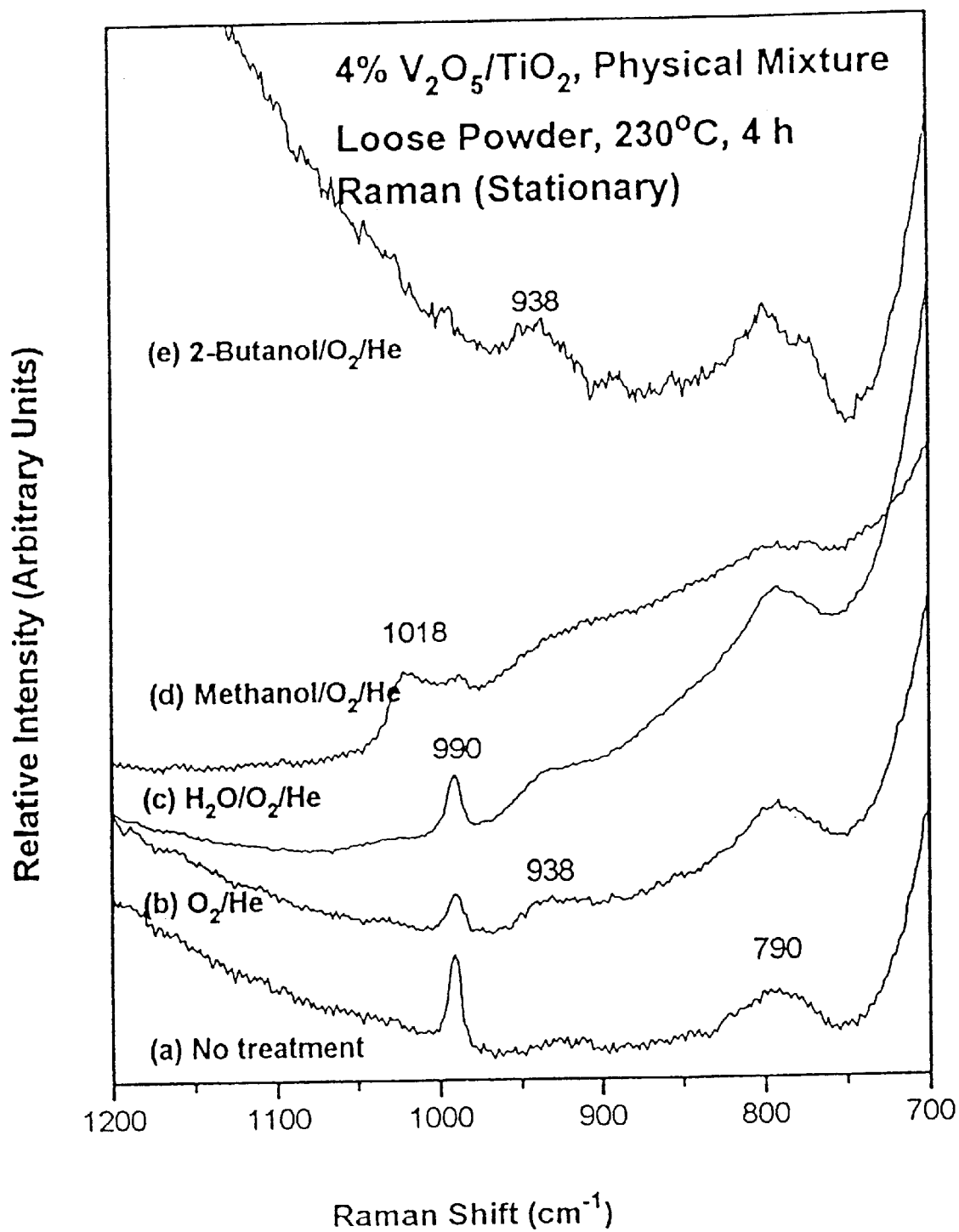
FIG. 15. Raman spectra (partially dehydrated by laser beam) of a 4% $V_2O_5/TiO_2$ physical mixture in powder form after four hours of alcohol oxidation and other gaseous stream treatment conditions at 230° C.: (a) no treatment, (b) $O_2/He$, (c) $H_2O/O_2/He$, (d) methanol oxidation, and (e) 2-butanol oxidation.

The influence of different gaseous environments on the spreading of $V_2O_5$ on $TiO_2$ is compared in the Raman spectra of FIG. 15. Exposure of the 4 wt % $V_2O_5/TiO_2$ physical mixture catalyst to the $O_2/He$ and $H_2O/O_2/He$ steams at 230° C. for 4 h resulted in a broad and ill-defined band at about 938 $cm^{-1}$ in addition to the sharp strong band at 990 $cm^{-1}$ due to crystalline $V_2O_5$ (FIGS. 15b–c). The Raman band 938 $cm^{-1}$ band has been assigned to a surface polymerized vanadium oxide species based on previous Raman and NMR studies.[19,29]

After the physical mixture was exposed to methanol and 2-butanol oxidation conditions at 230° C. for 4 h, the sharp 990 $cm^{-1}$ band of crystalline $V_2O_5$ almost completely disappeared and a broad band of considerable intensity at about 1018 and a weak band at 938 $cm^{-1}$ were observed for the sample after methanol oxidation (FIG. 15e) and only the 938 $cm^{-1}$ band was present in the sample after 2-butanol oxidation (FIG. 15e). The 1018 $cm^{-1}$ band is due to dehydrated surface vanadium oxide species, as a result of laser induced dehydration.[19]

Compared to other samples, the sample exposed to the 2-butanol oxidation condition possessed strong fluorescence in the 1000 $cm^{-1}$ region. The above results suggest that the efficiency of the reaction-induced spreading for the $V_2O_5/TiO_2$ physical mixtures follows the trend: methanol, 2-butanol>>water, oxygen.

Figure 16:
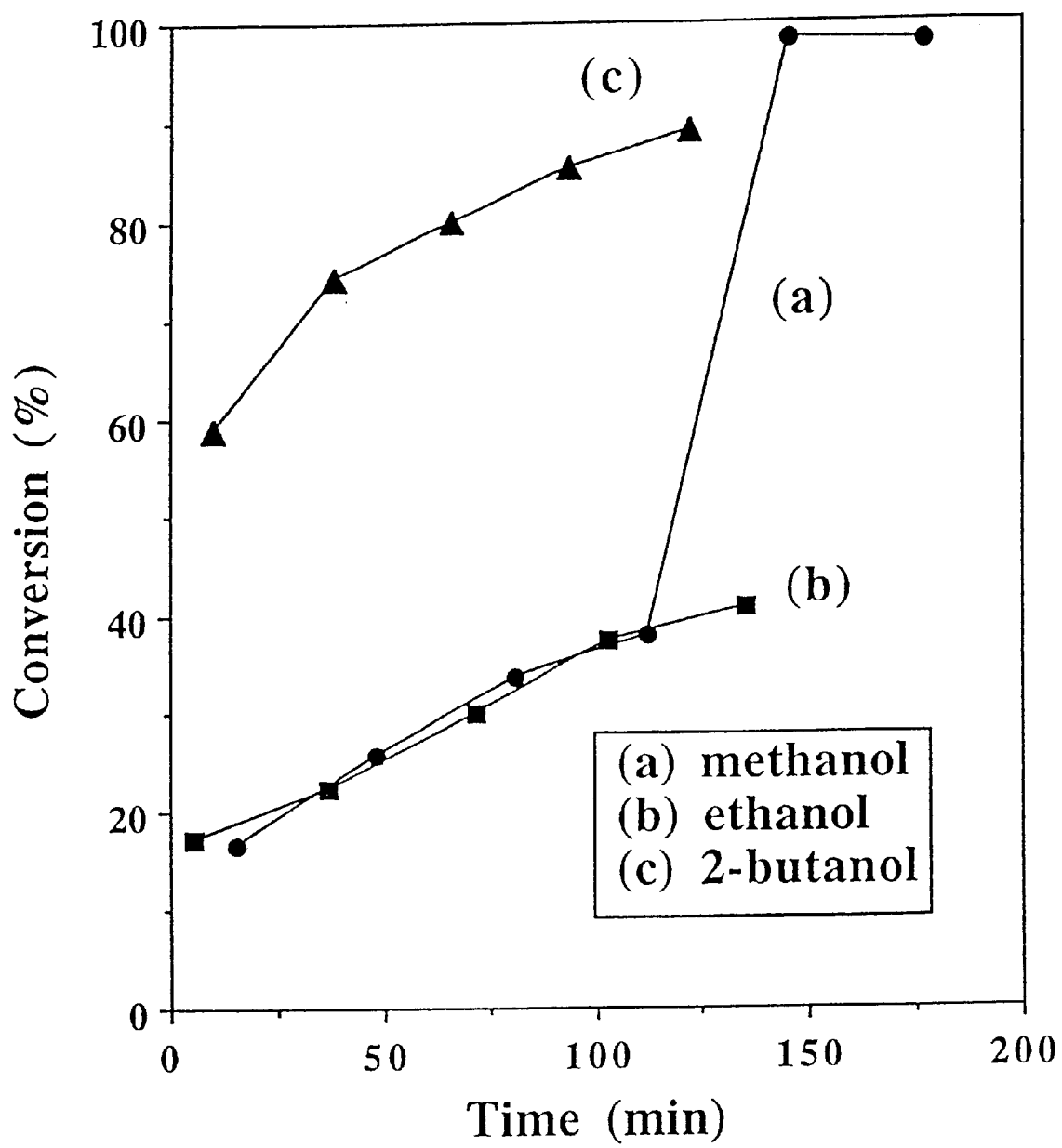
FIG. 16. Alcohol conversions over a 4% $V_2O_5/TiO_2$ physical mixture in powder form at 230° C. as a function of reaction time: (a) methanol oxidation, (b) ethanol oxidation, and (c) 2-butanol oxidation.

Alcohol conversions over the 4% $V_2O_5/TiO_2$ physical mixture catalyst are plotted against the reaction time and are shown in FIG. 16. The continuous increase of alcohol oxidation (methanol, ethanol, and 2-butanol) with time is consistent with the structural evolution of the 4 wt % $V_2O_5/TiO_2$ physical mire catalyst observed in the Raman studies. In this case, crystalline $V_2O_5$ transforms into the surface vanadium oxide species, which is the active site for alcohol oxidation. For methanol oxidation, the methanol conversion continuously increased from about 18 to 37% with time during the first 115 minutes and then exhibited a very sharp increase to ~100% at about 140 minutes. The jump in methanol conversion was accompanied by an increase in the catalyst bed temperature from 230° C. to 244° C. due to the exothermic heat of reaction.

Figure 17:
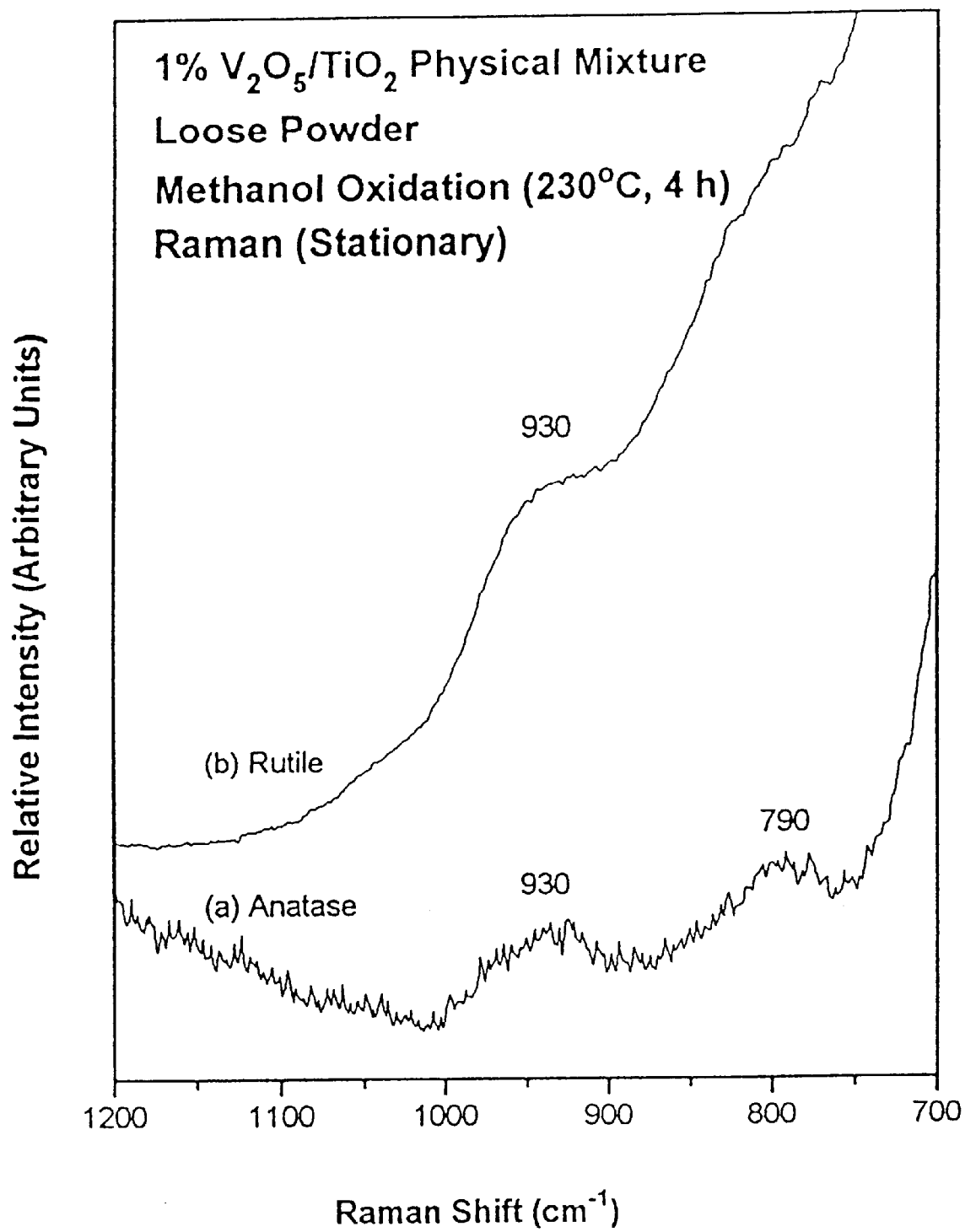
FIG. 17. Raman spectra (partially dehydrated by laser beam) of a 1% $V_2O_5/TiO_2$ physical mixture in powder form after four hours of methanol oxidation at 230° C.: (a) anatase, (b) rutile.

The reaction-induced spreading of $V_2O_5$ can occur on both $TiO_2$ (rutile) and $TiO_2$ (anatase) supports. FIG. 17 presents the Raman spectra of the 1 wt % $V_2O_5/TiO_2$ (rutile or anatase) physical mixtures after four hours of methanol oxidation at 230° C. A broad Raman band at about 930 cm$^{-1}$, characteristic of a polymerized surface vanadium oxide species,[19,29] is observed and the sharp 990 cm$^{-1}$ band of crystalline $V_2O_5$ is absent for both samples. This suggests that crystalline $V_2O_5$ has completely spread onto the surfaces of both rutile and anatase $TiO_2$ supports as surface vanadia species.

Example 7

Reaction Induced Spreading of $V_2O_5$ on $SnO_2$

Figure 18:
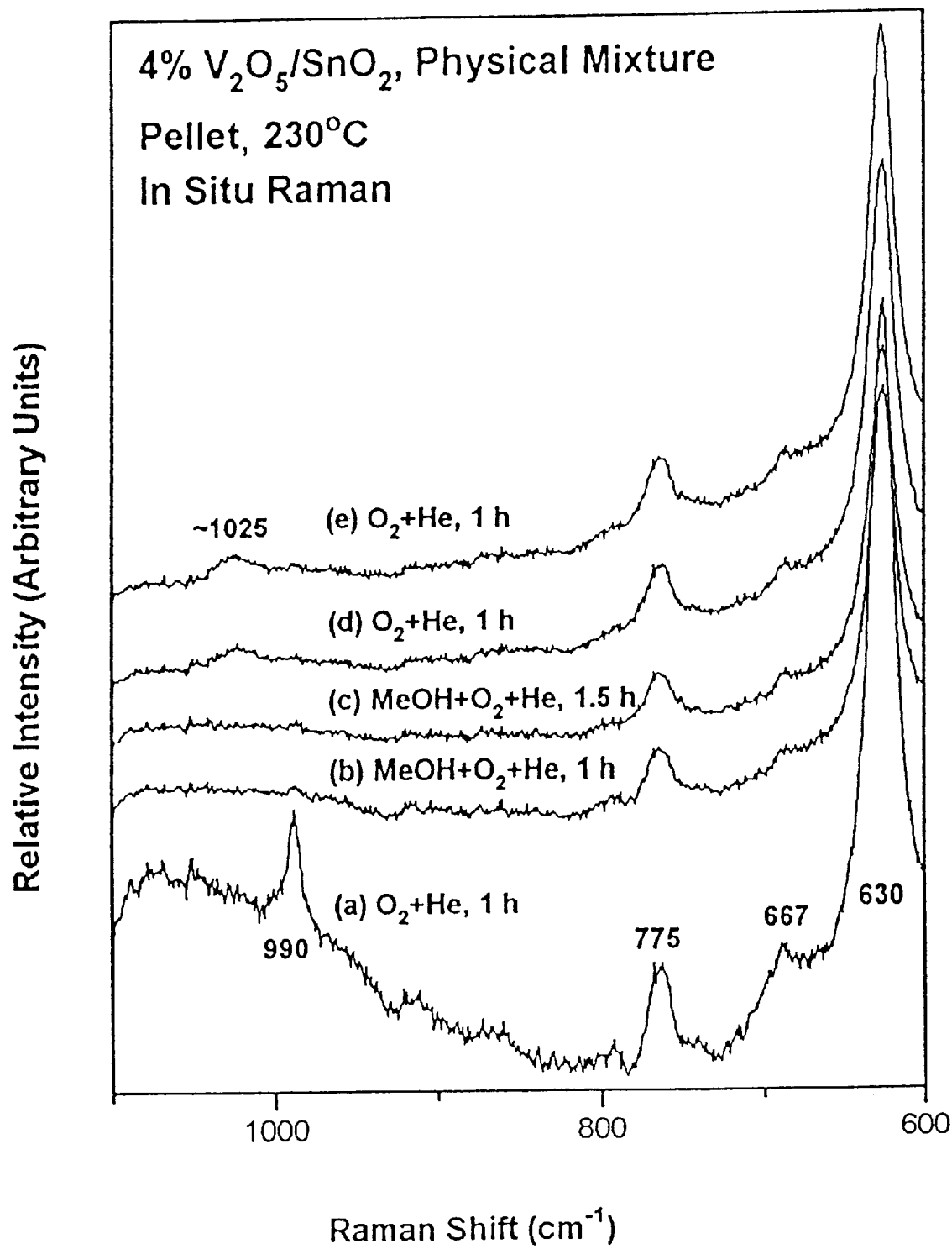
FIG. 18. In situ Raman spectra of a 4% $V_2O_5/SnO_2$ physical mixture in pellet form during methanol oxidation at 230° C.: (a) before methanol oxidation; (b) methanol oxidation, 1 h; (c) methanol oxidation, 1.5 h; (d) after oxidation, 0.5 h; and (e) after oxidation, 1 h.

The in situ Raman studies were also carried out on a 4 wt % $V_2O_5/SnO_2$ physical mixture catalyst during methanol oxidation at 230° C. (see FIG. 18). As previously described, the Raman bands at 766 and 630 cm$^{-1}$ are the characteristic features of the $SnO_2$ support. After 1.5 h of methanol oxidation, all the Raman bands related to the vanadia component of the catalyst disappeared, suggesting the vanadia component was reduced in the methanol oxidation environment. Reoxidation with $O_2$/He (16/84) at 230° C. for 0.5–1 hr reestablished a broad Raman band at 1025 cm$^{-1}$ due to the dehydrated surface vanadium oxide species. This experiment illustrates that reaction-induced spreading of crystalline $V_2O_5$ on the $SnO_2$ support occurred during methanol oxidation at a mild temperature. However, thermal spreading of $V_2O_5$ on $SnO_2$ was not observed to occur as reported by Honick et al.[22]

Example 8

Reaction Induced Spreading of $V_2O_5$ on $SiO_2$

Figure 19A:
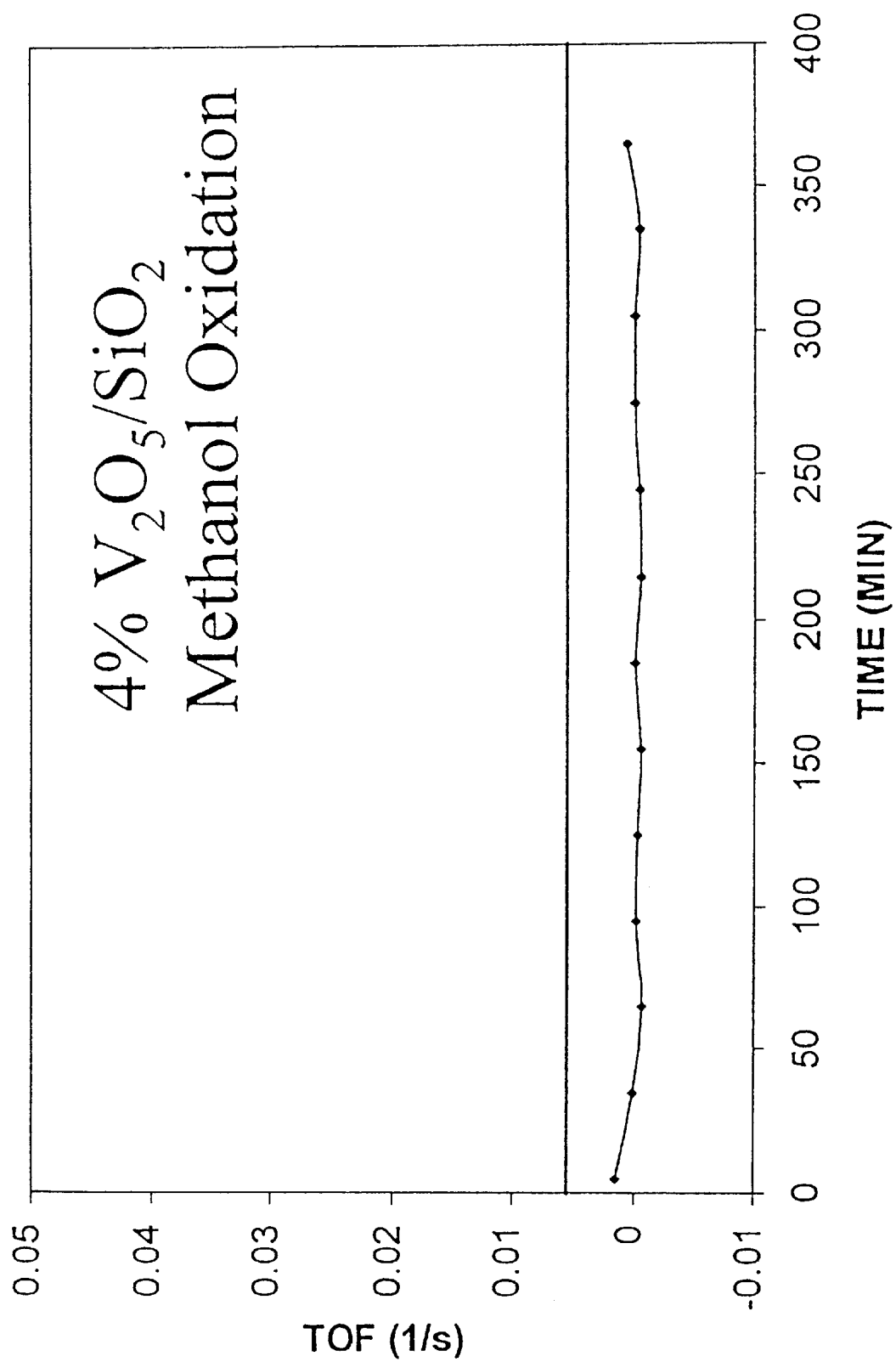
FIG. 19. (A) Plot of TOF versus the reaction time over a 4% $V_2O_5/SiO_2$ physical mixture catalyst in powder form in comparison with the initial TOF of a 4% $V_2O_5/SiO_2$ supported catalyst prepared by impregnation; (B) Raman spectra of the 4% $V_2O_5/SiO_2$ physical mixture catalyst before methanol oxidation (a) and after methanol oxidation (b).

Similar to the $MoO_3/SiO_2$ system, the reaction-induced spreading of $V_2O_5$ on $SiO_2$ is not achievable. The methanol oxidation TOFs as a function of reaction time for a 4 wt % $V_2O_5/SiO_2$ physical mixture catalyst at 230° C. are presented in FIG. 19(A). The constant TOFs, which are much lower than the initial TOF of a 4 wt % $V_2O_5/SiO_2$ catalyst prepared by impregnation, suggest that crystalline $V_2O_5$ did not transform into a surface vanadium oxide species. The corresponding Raman spectra of the 4% $V_2O_5/SiO_2$ physical mixture before and after methanol oxidation are presented in FIG. 19(B) and demonstrate that crystalline $V_2O_5$ has been completely removed from the physical mixture catalyst after methanol oxidation, also evidenced by the fact that the final catalyst exhibits the same color as pure $SiO_2$.

Example 9

Figure 20A:
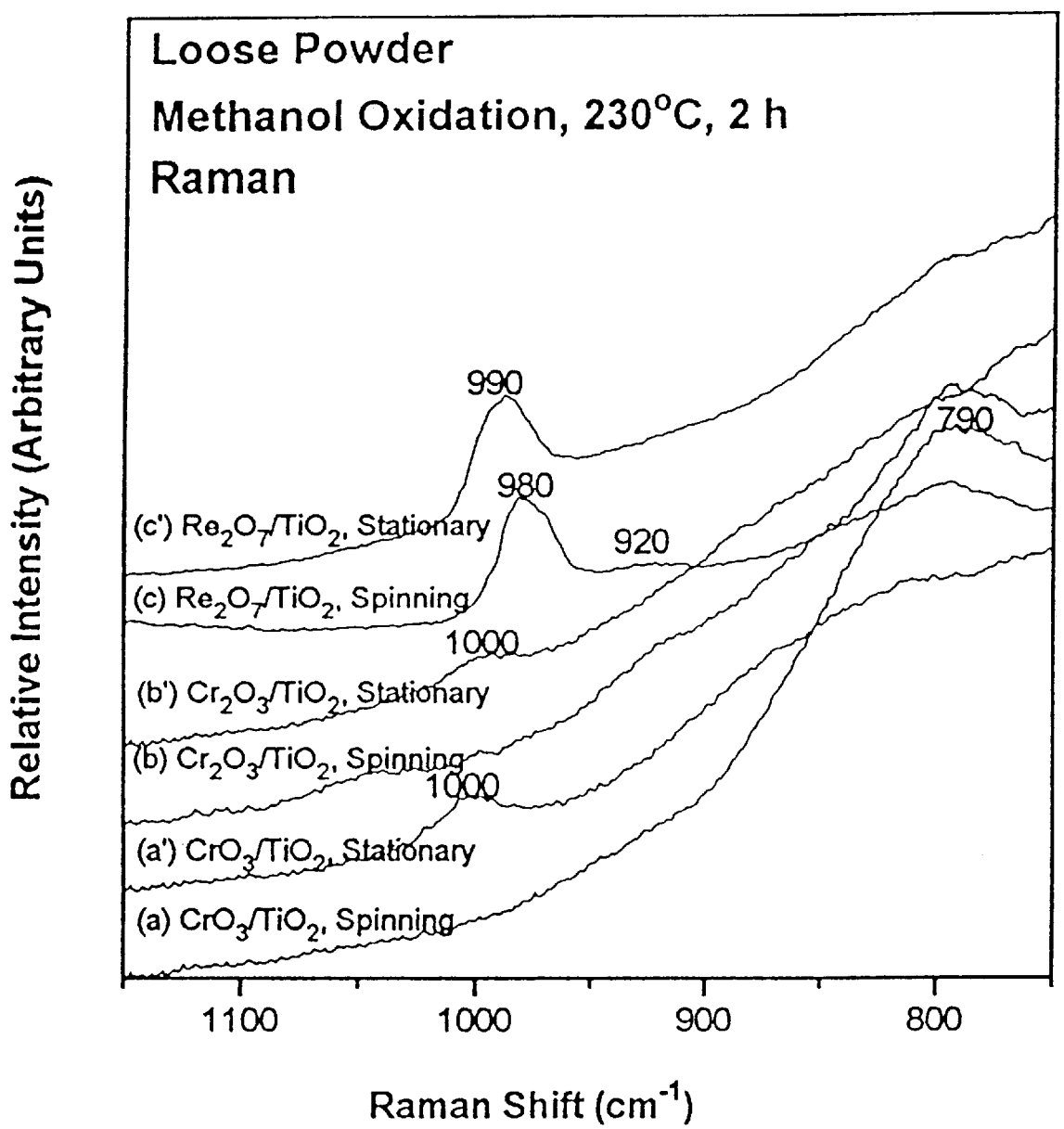
FIG. 20. Raman spectra of 4% $M_xO_y/TiO_2$ physical mixtures (M=Cr, Re, Nb, and W) in powder form after two hours of methanol oxidation at 230° C.

Reaction Induced Spreading of $CrO_3$, $Cr_2O_3$, $Re_2O_7$, $WO_3$, and $Nb_2O_5$ on $TiO_2$ Experiments were also performed to examine the reaction-induced spreading of other metal oxides ($CrO_3$, $Cr_2O_3$, $Re_2O_7$, $WO_3$, and $Nb_2O_5$) on the $TiO_2$ support (Degussa P-25). The Raman spectra for the 4% $M_xO_y$ (M=Cr, Re, W, and Nb)/$TiO_2$ physical mixtures after 2 h of methanol oxidation at 230° C. are presented in FIGS. 20(A) and (B). The Raman spectra were obtained by either spinning the samples or holding them stationary.

The Raman spectrum of the $CrO_3/TiO_2$ catalyst (spinning) exhibits only a band at 790 cm$^{-1}$ due to the $TiO_2$ support When the sample was stationary, dehydration induced by the laser beam resulted in a new band at ~1000 cm$^{-1}$, which was previously assigned to a dehydrated surface chromium oxide species.[30,31] Under hydrated conditions, this band would shift to ~880 cm$^{-1}$, but in this case the 880 cm$^{-1}$ band is masked by the high background in the 950–700 cm$^{-1}$ region of the catalyst.

Similarly to that observed for the $CrO_3/TiO_2$ catalyst, the $Cr_2O_3/TiO_2$ catalyst (stationary) also exhibits a weak band at ~1000 cm$^{-1}$, consistent with the presence of the dehydrated surface chromium oxide species. Interestingly, this result suggests that part of crystalline $Cr_2O_3$ has spread onto the $TiO_2$ surface during methanol oxidation and $Cr^{3+}$ has been oxidized to the surface $Cr^{6+}$ species. However, thermal spreading of $Cr_2O_3$ on supports hardly occurs due to its extremely high Tammann temperature (1081° C.).[9]

The Raman bands for the $Re_2O_7/TiO_2$ physical mixture after methanol oxidation occurs at ~980 and ~920 cm$^{-1}$. The 980 cm$^{-1}$ band shifts to ~990 cm$^{-1}$ due to partial dehydration of the stationary sample induced by the laser beam. This behavior is reversible, as demonstrated by a shift of the Raman band from 990 cm$^{-1}$ back to 980 cm$^{-1}$ when the sample is rotated. The current observation is consistent with the previous findings for the $Re_2O_7/Al_2O_3$ catalysts and reveals the ability of $Re_2O_7$ to readily spread onto the $TiO_2$ surface during methanol oxidation.[32]

Figure 20B:
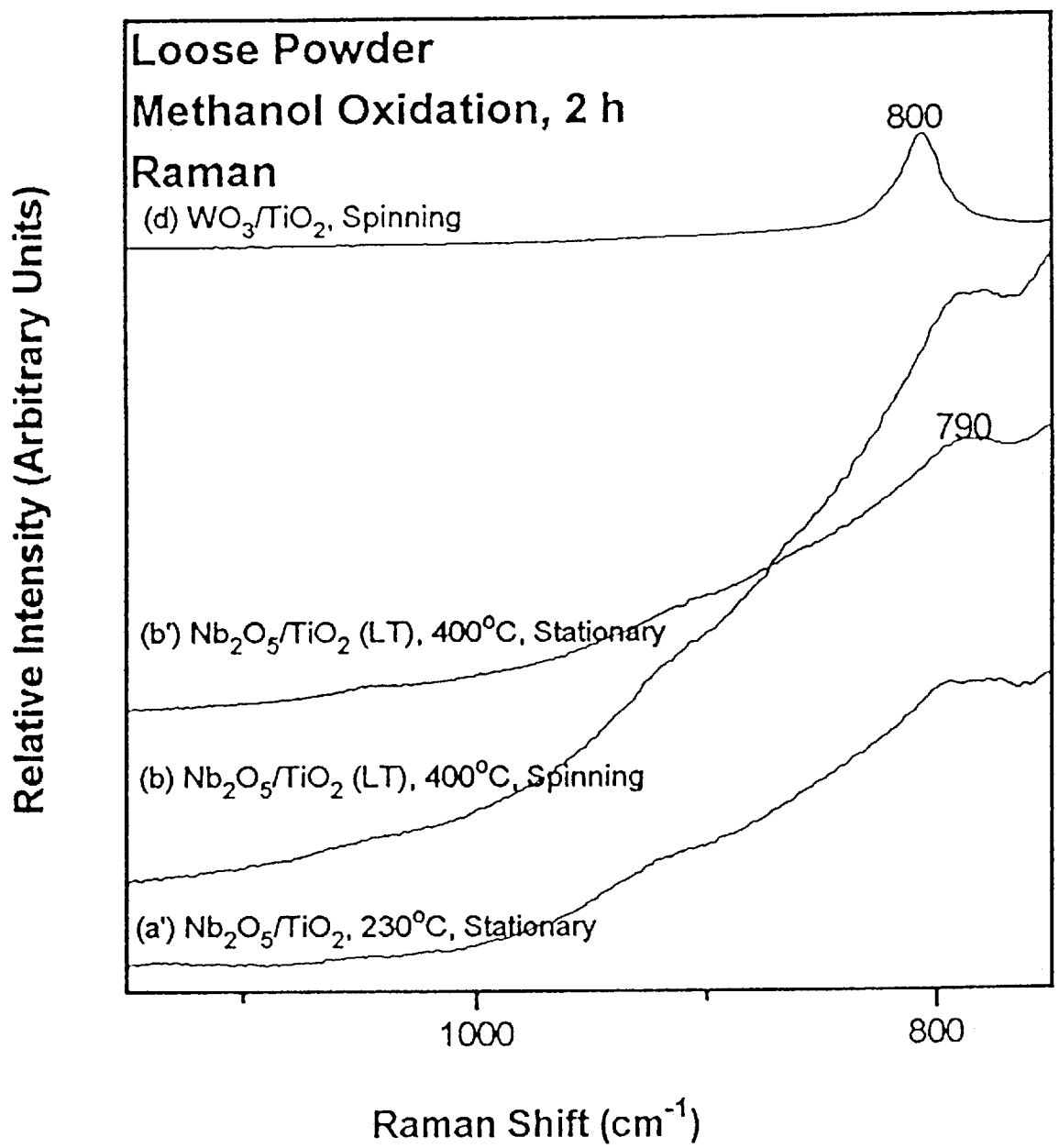

The Raman spectra of the 4% $Nb_2O_5/TiO_2$ physical mixture after two hours of methanol oxidation at 230 and 400° C. are presented in FIG. 20(B). The Raman spectra measured by spinning the samples or holding them stationary are almost identical, possessing only the ~790 cm$^{-1}$ band due to $TiO_2$. Absence of a ~980 cm$^{-1}$ band due to dehydrated surface niobium oxide species indicates that $Nb_2O_5$ did not spread onto the surface $TiO_2$ during methanol oxidation.[10,33]

The Raman spectra of the $WO_3/TiO_2$ catalyst exhibits very sharp bands at 800 and 713 cm$^{-1}$, which are characteristic of crystalline $WO_3$ particles. The Raman band due to the surface tungsten oxide species[34,35] (expected at 1010 cm$^{-1}$) is not observed, implying that reaction-induced spreading of $WO_3$ on $TiO_2$ does not occur for this system under these mild reaction conditions.

Discussion

A. Thermal Spreading

Thermal spreading of three-dimensional metal oxides and salts over oxide and zeolite supports as two-dimensional surface metal oxide species has been extensively researched for the past two decades and been reviewed in the recent catalysis literature.[8,9] The driving force for thermal spreading has received considerable attention from the thermodynamic point of view. A spontaneous process for one metal oxide spreading over surfaces of an oxide support requires the Gibbs free energy (DG) of the system negative (e.g., DG=DH−TDS+ADg<0, A—surface area of the oxide support, Dg—surface free energy change of the system). The well-established wetting principle for liquid-solid interaction has been applied to describe the thermal spreading of one component on an oxide support by Haber et al.[7] and Ruckenstein[36] on the assumption that the system DH and DS upon spreading are insignificant. The ability of an active phase to wet a support is determined by the following interfacial free energies: active phase-gas ($g_{ag}$), active phase-support ($g_{as}$), and support-gas ($g_{sg}$). When $Dg=g_{sg}+g_{as}-g_{ag}<0$, wetting of the support by the active phase occurs, where surface tension is the direct driving force for wetting of one solid by another solid. In contrast, Xie et al.[8] emphasizes the importance of DS upon spreading and includes the surface free energy change Dg into the term DH. The system DG is negative due to (a) dispersion of a metal oxide as a monolayer or submonolayer, if not a multilayer, onto surfaces of an oxide support would significantly increase entropy (DS>0) and (b) breaking chemical bonds of a metal oxide would be compensated by the formation of surface chemical bonds of the surface metal oxide species to the support surface (i.e., DH>>0). Concentration gradient of the active component is considered to be the direct driving force for spreading.

It is well known that surface diffusion or migration has played an important role in agglomeration, sintering, and active-component redistribution in heterogeneous catalysts.[37] Thermal spreading is believed to be related to surface migration or diffusion of one component over surfaces of an oxide support. High temperature is required for surface diffusion to overcome intrinsic resistance coming from the generally high lattice energies of active components. As a rule, thermal-spreading temperature must be higher than Tammann temperature in order for surface diffusion to occur.

When the 4% $MoO_3/TiO_2$ physical mixture is heated at 400–500° C., it is not surprising that a significant amount of crystalline $MoO_3$ has transformed into surface molybdenum oxide species (see FIG. 2) because the heating temperatures are much higher than the Tammann temperature of $MoO_3$ ($T_{Tamm}=261°$ C.). The higher the heating temperature, the more the crystalline $MoO_3$ transforms into the surface molybdenum oxide species due to higher surface diffusion or migration rate at higher temperatures. In contrast to prediction, thermal spreading of $V_2O_5$ on $TiO_2$ did not seem to occur after their physical mire was heated at 300–400° C. for 4 h in dry air (see FIGS. 4 and 5) although the heating temperatures were also much higher than the Tammann temperature of crystalline $V_2O_5$ (206° C.). Only a small amount of surface vanadium oxide species formed upon thermal treatment at 500° C. Conflicting results were reported in the literature regarding thermal dispersion of the $V_2O_5/TiO_2$ system. Haber et al.[39] and Honicke et al.[22] did observe significant spreading of $V_2O_5$ on $TiO_2$ after thermal treatment in dry air at 450° C. for 1 h or 500° C. for 48 h for their physical mixtures made by grinding in an agate mortar. In contrast Leyrer et al. showed that thermal spreading of $V_2O_5$ on $TiO_2$ did not occur after a hand-grinding physical mixture was thermally treated at 500° C. for 48 h in dry $O_2$.[18] Hausinger et al. demonstrated that the spreading tendency of $V_2O_5$ on $TiO_2$ was influenced by the preparation methods of their physical mixtures and the discrepancy in thermal dispersion of $V_2O_5$ on $TiO_2$ might relate to the mechanical mixing procedure.[23]

Thermal-spreading mechanism has been tentatively discussed in previous publications. Knozinger and coworkers[9] proposed an "unrolling-carpet mechanism" to describe thermal spreading, where mobile species from a "liquid-like" surface layer of a metal oxide across the grain boundaries onto an oxide support surface to form a monolayer film. Further migration of the mobile species over the monolayer film results in complete coverage of the whole support surface. Wang et al.[38] suggested that thermal spreading contains two steps: (1) mobile species leave surfaces of their own crystals for oxide support surfaces and (2) the mobile surface species further migrate and saturate the support surfaces. For compounds with high melting points, first step is rate-determining while for compounds with low melting points second step is rate-determining.

Thermal-spreading kinetics are influenced by metal oxide, oxide support, steam, oxidizing/reducing gaseous environment, mixing method, and surface impurity. Steam and oxidizing environments enhance the thermal spreading process. Under mildly reducing conditions, thermal spreading is significantly retarded due to usually the much higher Tammann temperatures of the corresponding reduced solid compounds. Under strong reducing conditions, formation of metals is completely unfavorable to spreading due to weak interaction between metal atoms and the oxide support.

It was noticed that mass transfer limitation is also an important factor to influence thermal-spreading rate. Mass transfer limitations exist in the pellet form of the $MoO_3/TiO_2$ physical mixture as demonstrated in FIG. 3 because thermal spreading hardly occurs. The presence of mass transfer limitations in catalyst pellets encountered in typical Raman and IR studies is a common phenomenon and the detailed results will be published in a separate paper.

B. Reaction-induced Spreading

Effect of temperature. The temperature range at which metal oxides spread allows for discrimination between reaction-induced spreading and thermal spreading. Thermal spreading of crystalline $MoO_3$ onto $TiO_2$ requires a temperature in excess of 300° C. since the Tammann temperature is 261° C. During methanol oxidation reaction, crystalline $MoO_3$ spreads onto the $TiO_2$ surface as a surface molybdenum oxide species at a temperature even as low as 100° C. (see FIG. 6).

The possibility of any hot spots in the fixed-bed reactor can be ruled out because the methanol conversion is extremely small (negligible at 100° C. and <5% at 150° C.) and, thus, the exothermic heat of reaction is negligible. This temperature is even much lower than the Tammann temperature of crystalline $MoO_3$, indicating that thermal-induced spreading does not account for this phase transformation and that a strong interaction between the gas phase components and crystalline $MoO_3$ must be occurring. Increasing the methanol oxidation reaction temperature from 100° C. to 230° C. leads to an increase in the spreading efficiency (see FIG. 6). Thus, reaction-induced spreading generally occurs at much lower temperature than thermal spreading of metal oxides.

The metal oxides ($MoO_3$, $V_2O_5$, and $Cr_2O_3$) do not thermally spread onto oxide supports at 230° C. because of their relatively high Tammann temperatures (listed in Table 1). Spreading of these metal oxides on the oxide supports ($TiO_2$ and $SnO_2$) during alcohol (methanol, ethanol, and 2-butanol) oxidation must correspond to the mechanism of reaction-induced spreading. For $CrO_3$ and $Re_2O_7$, thermal-induced spreading might also be occurring during methanol oxidation at 230° C. due to their relatively low Tammann temperatures (−38 and 12° C., respectively).

TABLE 1

Surface free energies, melting points and Tammann temperatures of metal oxides and oxide supports[9]

| Oxide | $\gamma/10^{-6}$ Jcm$^{-2}$ | $T_{melt}/°$ C. | $T_{Tam}/°$ C. |
|---|---|---|---|
| $CrO_3$ | — | 197 | −38 |
| $Re_2O_7$ | 3–4 | 297 | 12 |
| $V_2O_5$ | 8–9 | 690 | 209 |
| $MoO_3$ | 5–7 | 795 | 261 |
| $WO_3$ | 10 | 1474 | 600 |
| $Nb_2O_5$ | — | 1512 | 620 |
| $Cr_2O_3$ | — | 2454 | 1081 |
| $TiO_2$ | 28–38 | 1900 | 813 |
| $SnO_2$ | — | 1630 | 679 |
| $SiO_2$ | 60 | 1713 | 720 |
| $Al_2O_3$ | 68–70 | 2054 | 890 |
| MgO | 110–115 | 2800 | 1263 |
| ZnO | 90 | 1975 | 851 |
| $ZrO_2$ | 59–80 | 2715 | 1221 |

The reaction-induced spreading of $MoO_3$ and $V_2O_5$ on $TiO_2$ and $SnO_2$ also readily occurs in the pellet catalysts during methanol oxidation at 230° C. (see FIGS. 7, 11, 13, 18) in spite of mass transfer limitations in the pellets because of the rapid spreading of $MoO_3$ and $V_2O_5$ during methanol oxidation.

Effect of gaseous components. Several research groups found that the presence of water vapor influences the spreading rate of $MoO_3$,[18,40–42] $WO_3$,[18] and $V_2O_5$[18,43] on various oxide supports although moisture is not essential for thermal spreading at elevated temperatures (400–500° C.). It was proposed that volatile metal oxyhydroxide intermediates such as $MoO_2(OH)_2$, $WO_2(OH)_2$, $V_2O_3(OH)_4$, and $VO(OH)_3$ form in the presence of water vapor and, thus, may play an important role in the chemical transformation of these metal oxides. The present results presented in FIGS. 9 and 15 clearly show that the influence of water vapor on the spreading of $MoO_3$ and $V_2O_5$ was negligible when the physical mixtures were heated in a water-vapor saturated $O_2$/He flow at very mild temperatures such as 230° C. for a few hours.

The methanol oxidation reaction products are known to very weakly interact with metal oxides such as molybdates and vanadates. Adsorbed formaldehyde is readily displaced by the presence of moisture and methanol.[44,45] The interaction of carbon dioxide with molybdates and vanadates is extremely weak and adsorption is usually not even observed at room temperature.[46,47] Furthermore, reaction-induced spreading was observed during methanol oxidation even at 100° C. where no formaldehyde, carbon oxides, and water were produced. Thus, reaction-induced spreading is independent of the presence or absence of the methanol oxidation reaction products (HCHO, $H_2O$, CO, and $CO_2$).

Figure 19B:
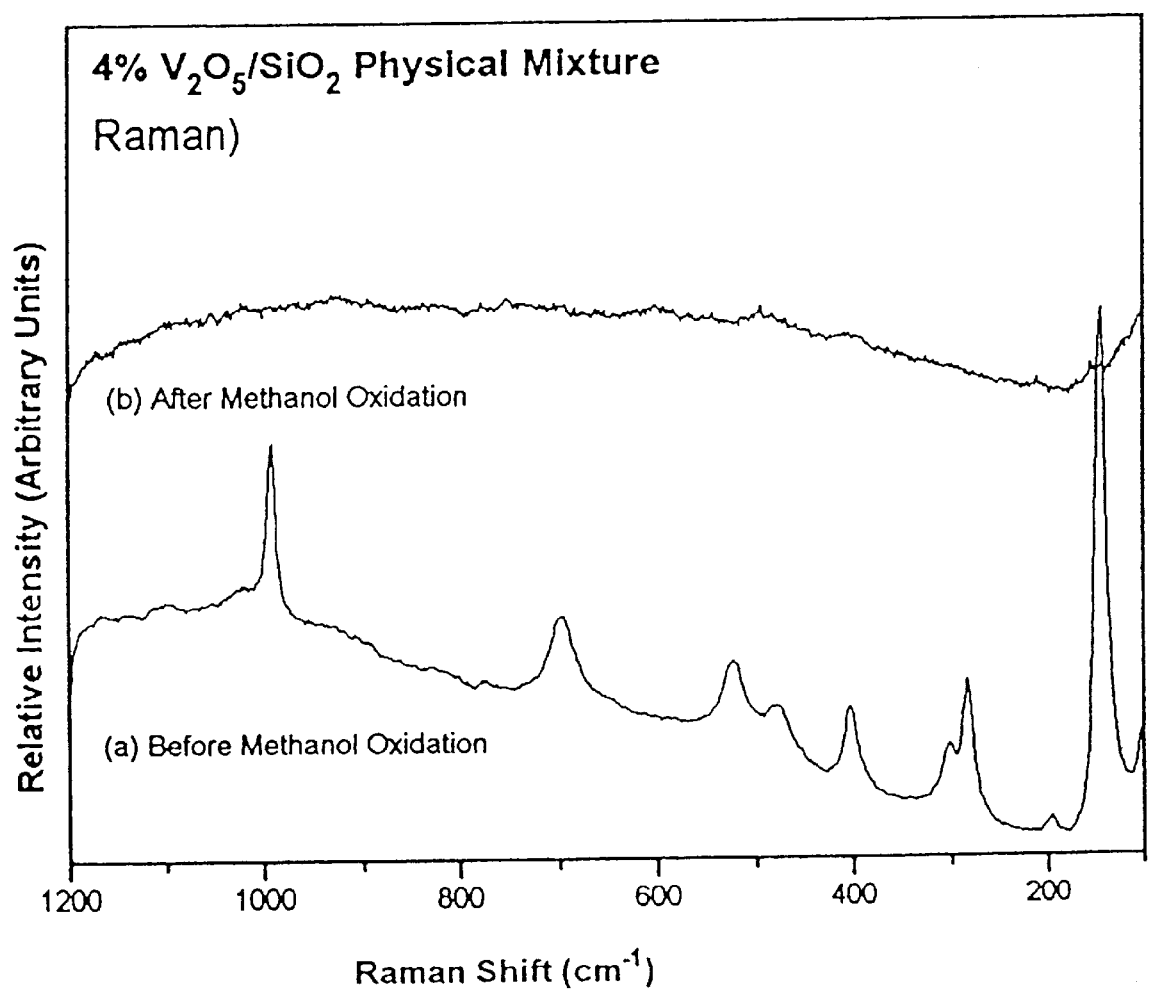

The interaction of methanol with molybdates and vanadates, however, is very strong and is much stronger than moisture since adsorption of methanol readily displaces adsorbed moisture.[44,45] Methanol oxidation over $V_2O_5/SiO_2$ and $MoO_3/SiO_2$ catalysts and crystalline $MoO_3$ and $V_2O_5$ results in the deposition of molybdena and vanadia at the cooler exit regions of the reactor due to the formation of volatile $Mo(OCH_3)_n$ and $V(OCH_3)_n$ complexes.[10] In this work, crystalline $MoO_3$ and $V_2O_5$ were essentially removed from their physical mixture catalysts during methanol oxidation to deposit at the cooler exit regions of the reactor (see FIGS. 12B and 19B). Thus, the low temperature dispersion of metal oxides over oxide supports during methanol oxidation is also related to the formation of the volatile metal-methoxy complexes. The methoxy complexes of vanadia and molybdena are well known and are liquids possessing high vapor pressures at room temperature.[48] The presence of the $TiO_2$ and $SnO_2$ supports adsorbs and stabilizes the volatile metal-methoxy complexes through formation of surface metal-methoxy species.

Similarly, the spreading of $MoO_3$ and $V_2O_5$ on $TiO_2$ induced by higher alcohols (ethanol and 2-butanol) during higher-alcohol oxidation is also due to the formation of volatile metal-alkoxy complexes. However, the kinetics of reaction-induced spreading of $MoO_3$ on oxide supports during oxidation of higher alcohols are significantly reduced relative to methanol oxidation (methanol>ethanol>2-butanol). The reduced spreading kinetics are related to the volatility and stability of the Mo-alkoxy complexes. As a rule of thumbs, the volatility and stability of the corresponding alkoxide compounds decreases when the carbon numbers in the alcohol chains increase.[48] The rate determining step during the catalytic oxidation of alcohols to their corresponding aldehydes or ketones involves breaking the alpha C—H bond of the surface alkoxy intermediates, and the stability of this bond decreases with the increasing numbers of carbon atoms coordinated to the alpha carbon.[45,49] Thus, the methoxy complex is more stable than the ethoxy complex, and the ethoxy complex is more stable than the 2-butoxy complex. Consequently, the greater volatility and stability of M-methoxy complexes are responsible for the greater efficiency of the reaction-induced spreading observed during methanol oxidation as well as the efficiencies of the different alcohols (methanol>ethanol>2-butanol).

Effect of supports. The current studies reveal that reaction-induced spreading of $MoO_3$ and $V_2O_5$ can readily occur on $TiO_2$ and $SnO_2$ supports, but is not observed for the $SiO_2$ support. The previous work on thermal spreading also claimed that surface metal oxide species could not be readily achieved on the $SiO_2$ support and, thus, conflicting results have been reported in the catalysis literature.[7,8,18,22,50] Several research groups demonstrated that salts and metal oxides (especially $MoO_3$) could spread onto $SiO_2$ when their physical mixtures were heated. On the contrary, other authors excluded the possibility of thermal spreading of metal oxides on $SiO_2$. Hence, alternate preparation methods such as impregnation and gas-phase grafting have been widely used to achieve monolayer dispersion of metal oxides onto the $SiO_2$ surface. Furthermore, the surface metal oxide species on $SiO_2$ is not thermally stable because physical mixtures of $SiO_2$-supported metal oxide species with other oxide supports results in complete transformation of the surface metal oxide species from $SiO_2$ to the other support upon thermal treatment.[51] The difficulty in wetting of the $SiO_2$ surface by other metal oxides must be due to the low interaction energy between the metal oxides and $SiO_2$ due to the hydrophobic character and low surface OH density and reactivity of the $SiO_2$ surface.[10] Therefore, the thermodynamic condition for wetting to occur cannot be satisfied although the surface free energies of the metal oxide and $SiO_2$ are favorable for wetting.

The stability of the surface metal oxide species on $SiO_2$ in presence of water and alcohol vapors is extremely low, reflected by the observation that water and methanol can transform the surface metal oxide species to crystalline bulk metal oxides through the formation of mobile and volatile metal oxide species.[12,26,52] During methanol oxidation over silica-supported catalysts, the transformation of surface metal oxide species to their bulk metal oxides is dominant, and its reverse process of reaction-induced spreading is essentially prohibited. Therefore, there is a good coherence between the reaction-induced spreading and the stability of surface metal oxide species on a specific support in the presence of alcohols. This relationship allows us to classify the oxide supports in two groups: group I is constituted only by $SiO_2$ on which the surface metal oxide species is not stable in the presence of alcohols and reaction-induced spreading does not occur during alcohol oxidation reactions, and group II is constituted by $TiO_2$, $SnO_2$, $Al_2O_3$, $ZrO_2$, and $CeO_2$ that favor and stabilize the surface metal oxide species in the presence of alcohols and reaction-induced spreading can readily occur during alcohol oxidation reactions.

The specific $TiO_2$ phase (anatase and rutile) does not influence the reaction-induced spreading of $V_2O_5$ because the same surface vanadium oxide species is present on both anatase and rutile $TiO_2$ supports after methanol oxidation (FIG. 17). Previous structure-reactivity studies also reveal that the $TiO_2$ phases (anatase, rutile, brookite and B) do not influence the molecular structure and reactivity of the surface vanadium oxide species.[53]

Effect of metal oxides. Metal oxides with lower melting points and Tammann temperatures (e.g. $CrO_3$, $MoO_3$, $V_2O_5$, and $Re_2O_7$) readily spread onto $TiO_2$ as surface metal oxide species during methanol oxidation at 230° C. In contrast, metal oxides with higher melting points and Tammann temperatures (e.g. $WO_3$ and $Nb_2O_5$) do not readily transform into the surface metal oxide species on $TiO_2$ during methanol oxidation reactions at the same temperature or even 400° C. (see FIG. 20B). The metal oxides with higher melting points imply a higher stability of crystalline structures due to their high cohesive or lattice energies. Transformation from a crystalline state into an amorphous surface metal oxide species requires a much stronger interaction between the metal oxides and the gaseous components as well as the higher stability of the metal-alkoxide complexes, which were not fulfilled in current methanol reaction conditions.

The oxidation state of the metal cations in the metal oxides is not as important in reaction-induced spreading as in thermal spreading, which basically depends on the Tammann temperature of the crystalline metal oxide phases. Thermal spreading is significantly retarded for reduced metal oxide phases that usually possess very high Tammann temperatures.[9,39] However, essentially complete dispersion of $V_2O_5$ on $TiO_2$ was observed during methanol oxidation even though the in situ Raman spectra revealed that the vanadia was reduced under the reaction conditions (see FIG. 13). Essentially complete dispersion of $MoO_3$ on $TiO_2$ was also observed after treatment of the catalyst in an oxygen-free methanol environment (see FIG. 6). Furthermore, reaction-induced spreading of $Cr_2O_3$ on $TiO_2$ was observed to occur during methanol oxidation even at 230° C. (see FIG. 20). In view of the extremely high Tammann temperature of $Cr_2O_3$ (1081° C.), thermal spreading appears to be infeasible at such a mild temperature. Fouad et al. previously suggested that $CrO_2$ ($T_{Tam}$=−36° C.) might be the mobile phase assisting the spreading process of $Cr_2O_3$ under certain circumstances.[54] Thus, reaction-induced spreading of $Cr_2O_3$ during methanol oxidation might be assisted by trace amounts of surface $CrO_3$ and/or $CrO_2$ that have low Tammann temperatures (−38 and −36° C., respectively) through facilitating the formation of Cr-methoxy complexes. Therefore, the oxidation states of the metal oxides does not significantly influence the kinetics of reaction-induced spreading of crystalline metal oxides and the reaction-induced spreading must proceed by mechanisms different from thermal spreading.

Mechanisms of Reaction-induced Spreading

Figure 21:
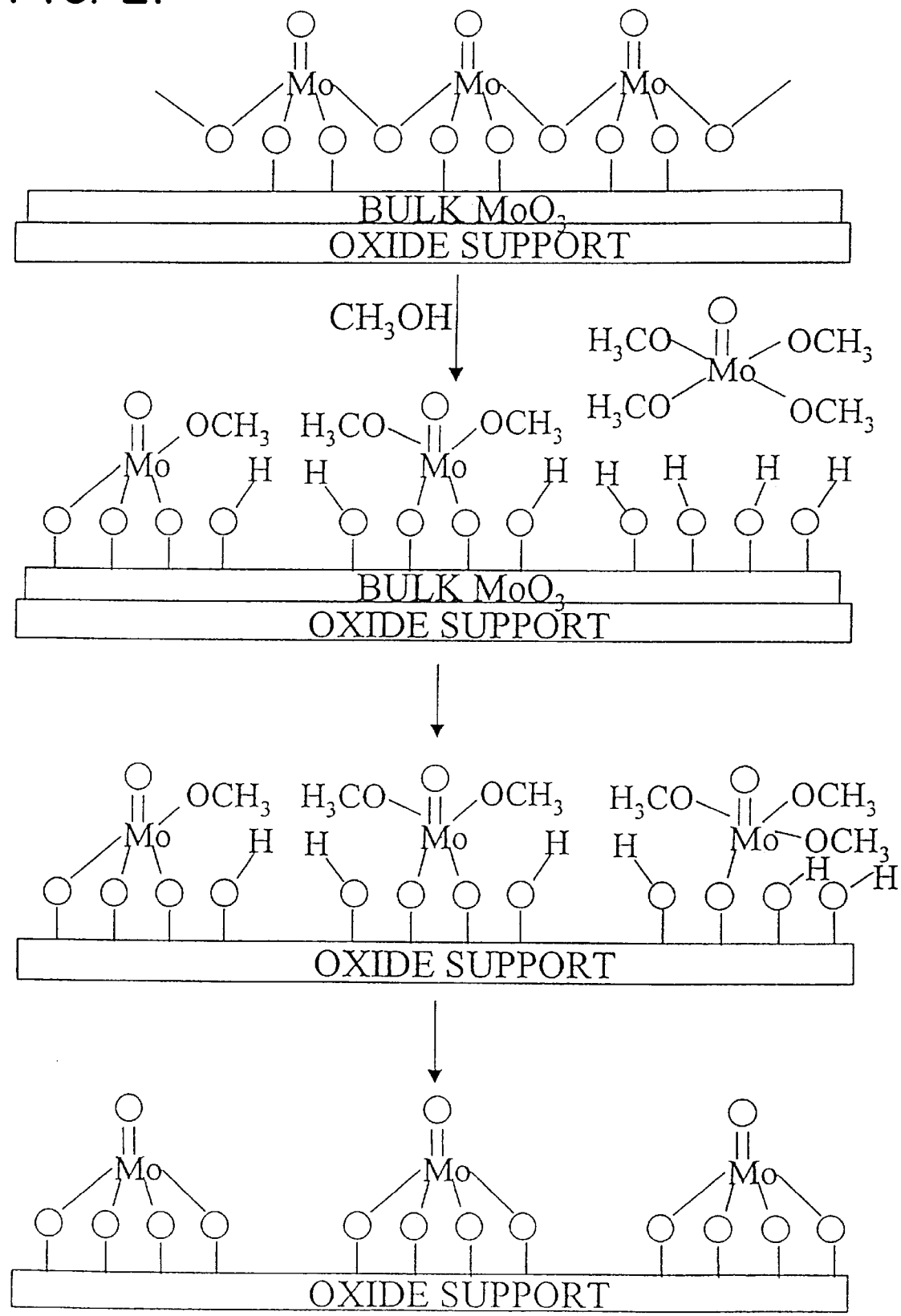
FIG. 21. Schematic of reaction-induced spreading of $MoO_3$ assisted by methanol.

As discussed above, alcohols (methanol, ethanol, and 2-butanol) are the functional compounds that are responsible for the efficient transformation of crystalline metal oxides into the two-dimensional surface metal oxide species on oxide supports. A schematic of reaction-induced spreading of $MoO_3$ assisted by methanol is shown in FIG. 21. The following steps are involved in reaction-induced spreading: (a) attack of the bridging Mo-O-Mo bonds of crystalline $MoO_3$ by methanol molecules to form a molybdenum methoxy complexes, (b) transfer of the molybdenum methoxy complexes from $MoO_3$ to the oxide support surface, (c) transformation of the molybdenum methoxy complexes into a surface molybdenum oxide species stabilized on the oxide support surface.

It is well known that metal-methoxy species are the reaction intermediates of methanol oxidation over supported metal oxide catalysts.[55] The mobility of the molybdenum methoxy species is directly related to the number of methoxy groups attached to the molybdenum cation. The more the methoxy group, the more mobile the surface molybdenum methoxy species. When a molybdenum cation connects to four methoxy groups, a volatile molybdenum methoxide forms.

The dramatic temperature difference between reaction-induced spreading and thermal-induced spreading is directly due to the formation of the mobile molybdenum methoxy complexes during methanol oxidation. Thus, step (b) can be considered in the following two ways: (I) transport by surface diffusion or migration in a concentration gradient of the surface molybdenum methoxy species, and (ii) gas-phase volatilisation/readsorption of the volatile molybdenum methoxide. Direct evidence for (ii) comes from the observation that $MoO_3$ and $V_2O_5$ can transfer from the reactor to the cooler exit of the reactor during methanol oxidation (see FIGS. 12B and 19B).

In the physical mixture catalysts of metal oxides and oxide supports (e.g., $TiO_2$ and $SnO_2$), the oxide supports can trap the gas-phase molybdenum or vanadium methoxide to react with their surface hydroxyls,[10] resulting in formation of surface metal-methoxy species. Therefore, reaction-induced spreading kinetics are essentially related to the volatility and stability of the metal alkoxy complexes. The volatility and stability of metal-alkoxides follows the trend: methoxy>ethoxy>2-butoxy. The higher the volatility and stability of the methoxy complex, the more readily the transformation from bulk to surface species occurs. Thus, methanol serves as a reagent that exhibits the highest efficiency for reaction-induced spreading among alcohols.

The mechanism of reaction-induced spreading corresponds to a mechanism previously proposed for thermal spreading.[38] The authors assumed thermal spreading to contain two steps: (a) a "molecule" leaves its metal oxide surface for the external surface of a support and (b) the "molecule" further diffuses on the support surface. It was found that for solid compounds with high melting points, (a) is the rate-determining step, and that for compounds with low melting points, (b) is the rate-determining step. The presence of alcohols can greatly facilitate the first step as well as the second step by formation of mobile metal-alkoxy species or volatile alkoxide as transporting intermediates and, thus, the activation energy and temperature required for spreading are dramatically decreased with assistance of alcohols.

Catalytic Properties

It has been well documented that the surface metal oxide species of the supported metal oxide catalysts primarily serves as the active components and controls the catalytic properties.[6] The current studies clearly demonstrate that the methanol oxidation activity and the formaldehyde selectivity of the binary oxide physical mixture catalysts progressively approach the catalytic properties of their corresponding supported metal oxide catalysts prepared by impregnation (see FIGS. 8 and 14).

The changes in the catalytic properties as a function of reaction time correspond to the phase transformation of the active components from three-dimensional metal oxides into two-dimensional surface metal oxide species on oxide supports (e.g., $TiO_2$ and $SnO_2$). The final methanol TOF and formaldehyde selectivity of the 4% $V_2O_5/TiO_2$ physical mixture catalyst are essentially the same as those of the 4% $V_2O_5/TiO_2$ supported catalyst prepared by impregnation, suggesting that all of the crystalline metal oxides spread onto the $TiO_2$ surface as surface vanadium oxide species. The Raman spectrum of the final catalyst further confirms the complete spreading of crystalline $V_2O_5$. However, the changes in catalytic properties with reaction time were not observed for the physical mixture catalysts comprised of metal oxides and the $SiO_2$ support because surface metal oxide species did not form on the $SiO_2$ surface during methanol oxidation (see FIGS. 12 and 19).

The data in FIGS. 10 and 16 also reveal that the conversions of ethanol and 2-butanol oxidation reactions over the physical mixture catalysts increase with reaction time, implying occurrence of an analogous phase transformation from three-dimensional metal oxides into active surface metal oxide species during the alcohol oxidation reactions.

In the catalysis literature, synergetic effects involving oxygen spillover of active species in selective oxidations over mixed metal oxide catalysts have been proposed to play a determining role in catalysis.[56,57] This phenomenon might relate to reaction-induced spreading, where oxygen as well as metal species of one metal oxide migrate or "spill over" to the surface of another metal oxide. The possibility that reaction-induced spreading occurs during selective oxidations over physical mixture catalysts needs to be carefully examined and eliminated before other mechanisms are proposed to explain the observed synergetic effects of physical mixture catalysts.

Implications to Commercial Application

A very important consequence of reaction-induced spreading of metal oxides during alcohol oxidation is that the catalyst preparation method of many supported metal oxide systems is not critical since the same surface metal oxide species will form during oxidation reactions (especially methanol oxidation).[19,39,57]

The current findings that reaction-induced spreading of metal oxides on oxide supports can occur during oxidation reactions (especially methanol) at very low temperatures also have important implications for commercial applications. They provide an alternate and unique route to the preparation and manufacture of supported metal oxide catalysts, where handling a large volume of salt solution in aqueous impregnation and coprecipitation methods and using expensive precursors in alkoxide impregnation can be avoided and, therefore, offers an environmental benign and economic process for catalyst preparation.

Furthermore, catalyst deactivation also relates to the reaction-induced spreading phenomenon. For example, the oxidation of methanol to formaldehyde is industrially conducted with $Fe_2(MoO_4)_3 \cdot MoO_3$ catalysts that contain excess $MoO_3$. The strong interaction between methanol and $MoO_3$ results in the stripping of the molybdena from the catalyst and its deposition as crystalline $MoO_3$ needles at the bottom of the reactor where the temperatures are somewhat low. This volatilization phenomenon is responsible for catalyst deactivation and pressure build-up in such commercial reactors.[59] The opposite behavior of reaction-induced spreading is observed during methanol oxidation over $MoO_3/SiO_2$ catalysts at 230° C. The strong interaction of methanol with Mo and the weak interaction between surface molybdena species and the silica support results in agglomeration and crystallization of the surface molybdena species to beta-$MoO_3$ particles during methanol oxidation.[26,60]

Conclusions

A new phenomenon of reaction-induced spreading of metal oxides on oxide supports as a two-dimensional metal oxide overlayer is observed during alcohol oxidation at temperatures much lower than that required for thermal spreading. The reaction-induced spreading proceeds through surface diffusion and volatilization/readsorption of metal-alkoxy complexes. Many factors (e.g., temperature, gaseous component, oxide support and metal oxide) were found to influence the transformation rate of three-dimensional crystalline metal oxides into two-dimensional surface metal oxide species. Increasing the reaction temperature increases the spreading rate during methanol oxidation.

The gaseous components assist the metal oxide spreading in the following order: methanol>>ethanol>2-butanol, water>>oxygen, formaldehyde, and carbon dioxide. The mechanism of reaction-induced spreading relates to the formation of the mobile surface metal-alkoxy species and the volatile metal alkoxides, and their subsequent transport through surface diffusion and volatilization/readsorption. The highest efficiency of methanol-assisted spreading corresponds to the highest volatility and stability of the metal-methoxy complexes.

There are two categories of oxide supports: (1) $SiO_2$, on which the reaction-induced spreading does not occur and the reverse process of transformation of surface metal oxide species to crystallites is dominant; (2) oxide supports (e.g., $TiO_2$, $Al_2O_3$, $Nb_2O_5$, $ZrO_2$, and $SnO_2$), on which the reaction-induced spreading of metal oxides (e.g., $CrO_3$, $Cr_2O_3$, $MoO_3$, $V_2O_5$, and $Re_2O_7$) readily occurs during alcohol oxidation at mild temperatures. $WO_3$ and $Nb_2O_5$ do not readily transform into surface metal oxide species during alcohol oxidation due to their high adhesive and lattice energies. The oxidation states of the spreading metal oxides do not significantly influence the reaction-induced spreading.

The catalytic properties were found to correspond to the phase transformation of crystalline metal oxides into the surface metal oxide species that are the active sites for methanol oxidation. Both methanol oxidation activity and formaldehyde selectivity of the physical mixture catalysts can reach those of their corresponding supported metal oxide catalysts. Supported metal oxide catalysts can be made using reaction-induced spreading as an alternate and unique route to avoid handling a large volume of salt solution in coprecipitation and using expensive precursors in alkoxide impregnation.

References (1) Gates, B. C.; Katzer, J. R; Schuit, G. C. A. *Chemistry of Catalytic Processes*; McGraw-Hill: New York, 1979.
(2) Topsoe, H. *Surface Properties and Catalysis by Non-Metals*; Bonnelle, J. P., Delmon, B., Derouane E., Eds.; Reidel, Dordrecht: Boston, 1983; pp 329.

(3) Bond, G. C.; Vedrine, J. C. *Catal. Today* 1994, 20, 1.
(4) Centi, G. *Appl. Catal. A*, 1996, 147, 267.
(5) Bosch, H; Janssen, F. *Catal. Today* 1988, 2, 369.
(6) Wachs, I. E. *Catalysis* 1997, 13, 37.
(7) Haber, J. *Pure & Appl. Chem.* 1984, 56, 1663.
(8) Xie, Y. C.; Tang, Y. Q. *Adv. Catal.* 1990, 31, 1.
(9) Knozinger, H.; Taglauer, E. *Catalysis* 1993, 10, 1.
(10) Wachs, I. E. *Catal. Today* 1996, 27, 457.
(11) Gasior, M; Haber, J.; Machej, T. *Appl. Catal.* 1987, 33, 1.
(12) Cavalli, P.; Cavani, F.; Manenti, I.; Trifiro, F. *Ind. Eng. Chem. Res.* 1987, 26, 639.
(13) Deo, G.; and Wachs; I. E. *J. Catal.* 1994, 146, 335.
(14) Vuurman, M. A.; Hirt, A. M.; Wachs, I. E. *J. Phys. Chem.* 1991, 95, 9928.
(15) Haber, J.; Machej, T.; Grabowski, R. *Solid State Ionics* 1989, 32/33, 887.
(16) Xie, Y.; Gui, L.; Liu, Y.; Zhao B.; Yang, N.; Zhang, Y.; Guo, Q.; Duan L.; Huang, H.; Cai, X.; Tang, Y. *Proc. 8th Intern. Congr. Catal.*; Dechema, Frankfurt, and Verlag Chemie: Weinheim, 1984; vol. V, pp 147.
(17) Margraf, R.; Leyrer, J.; Taglauer, E.; Knozinger, H. *React. Kinet. Catal. Lett.* 1987, 35, 261.
(18) Leyrer, J.; Margraf, R.; Taglauer E.; Knozinger H. *Surf. Sci.* 1988, 201, 603.
(19) Machej, T.; Haber, J.; Turek A. M.; Wachs, I. E. *Appl Catal.* 1991, 70, 115.
(20) Haber, J. *Surface Properties and Catalysis by Non-Metals*; Bonnelle, J. P., Delmon, B., Derouane E., Eds.; Reidel, Dordrecht: Boston, 1983; pp 1.
(21) Haber, J.; Machej, T.; Czeppe, T. *Surf. Sci.* 1985, 151, 301.
(22) Honicke, D.; Xu, J. *J. Phys. Chem.* 1988, 92, 4699.
(23) Hausinger, G.; Schmelz, H.; Knozinger, H. *Appl. Catal.* 1988, 39, 267.
(24) Hu, H.; Wachs, I. E. *J. Phys. Chem.* 1995, 99, 10911.
(25) Stampfl, S. R.; Chen, C.; Dumesic, J. A.; Niu, C.; Hill, Jr., C. G. *J. Catal.* 1987, 105, 445.
(26) Jehng, J. M.; Hu, H.; Gao, X.; Wachs, I. E. *Catal. Today* 1996, 28, 335.
(27) Wachs, I. E.; Jehng, J. M.; Deo, G.; Wechen, B. M.; Guliants, V. V.; Benziger, J. B. *Catal. Today* 1996, 32, 47.
(28) Went, G.; Oyama, S. T.; Bell, A. T. *J. Phys. Chem.* 1990, 94, 4240.
(29) Eckert, H.; Wachs, I. E. *J. Phys. Chem.* 1989, 93, 679.
(30) Hardcastle, F. D.; Wachis, I. E. *J. Mol. Catal.* 1988, 46, 173.
(31) Vuurman, M. A.; Wachs, I. E.; Stufkens, D. J.; Oskamn, A. *J. Mol. Catal.* 1993, 80, 209.
(32) Hardcastle, F. D.; Wachs, I. E. *J. Mol. Catal.* 1988, 46, 15.
(33) Jehing, J. M.; Wachs, I. E. *Catal. Today* 1993, 16, 417.
(34) Deo, G.; Wachs, I. E. *J. Phys. Chem.* 1991, 95, 5889.
(35) Kim, D. S.; Ostromecki, M.; Wachs, I. E. *J. Mol. Catal. A* 1996, 106, 93.
(36) Ruckenstein, E.; Lee, S. H. *J. Catal.* 1987, 104, 259.
(37) Wanke, S. E.;, Flynn, P. C. *Catal. Rev. Sci. Eng.* 1975, 12, 93.
(38) Wang, C. B.; Xie, Y. C.; Tang, Y. Q. *Science in China* 1994, 37, 1458.
(39) Haber, J.; Machej, T.; Serwicka, E. M.; Wachs, I. E. *Catal. Lett.* 1995, 32, 101.
(40) Margraf, R.; Leyrer, J.; Taglauer, E.; Knozinger, H. *Surface Sci.* 1987, 189/190, 842.
(41) Leyrer, J.; Zaki, M. I.; Knozinger, H. *J. Phys. Chem.* 1986, 90, 4775.
(42) Leyrer, J.; Mey, D.; Knozinger, H. *J. Catal.* 1990, 124, 349.
(43) Shan, S.; Honicke, D. *Chem.-Ing.-Techn.* 1989, 61, 321.
(44) Cheng, W. H. *J. Catal.* 1996, 158, 477.
(45) Holstein, W.; Machiels, C. J. *J. Catal.* 1996, 162, 118.
(46) Segawa, K.; Hall, W. K. *J. Catal.* 1982, 77, 221.
(47) Turek, A. M.; Wachs, I. E.; DeCanio, E. *J. Phys. Chem.* 1992, 96, 5000.
(48) Bradley, D. C.; Mehrotra, R. C.; Gaur, D. P. *Metal Alkoxides*; Academic Press: New York, 1978.
(49) Fameth, W. E.; Staley, R. H.; Sleight, A. W. *J. Am. Chem. Soc.* 1986, 108, 2327.
(50) Knozinger, H. *Mater. Sci. Forum*, 1988, 25/26, 223.
(51) Jehng J. M.; Wachs, I. E.; Weckhuysen, B. M.; Schoonheydt, R. A. *J. Chem. Soc., Faraday Trans.* 1994, 91, 953.
(52) Wang, C. B.; Deo, G.; Wachs, I. E. *J. Catal.*, submitted.
(53) Deo, G.; Turek A. M.; Wachs, I. E. ; Machej, T.; Haber, J.; Das, N.; Eckert, H.; Hirt, A. M. *Appl. Catal. A* 1992, 91, 27.
(54) Fouad, N. E.; Knozinger, H.; Ismail H. M.; Zaki, M. I. *Z. Phys. Chem.* 1991, 173, 201.
(55) Tatibouet, J. M. *Appl. Catal. A* 1997, 148, 213.
(56) Ruiz, P.; Delmon, B. *Catal. Today* 1988, 3, 199.
(57) Delmon, B.; Froment, G. F. *Catal. Rev.-Sci. Eng.* 1996, 38, 69.
(58) Centi, G.; Pinelli, D.; Trifiro, F.; Ghoussoub, G.; Guelton, M.; Gengembre, L. *J. Catal.* 1991, 130, 238.
(59) Pearce, R.; Patterson, W. R. *Catalysis and Chemical Process*; Wilay: New York, 1981.
(60) Banares, M.; Hu, H.; Wachs, I. E. *J. Catal.* 1994, 150, 407.

While various alterations and permutations of the invention are possible, the invention is to be limited only by the following claims and equivalents.

We claim:

1. A method for forming an aldehyde from an alcohol and oxygen comprising:
  contacting a reactant stream containing an alcohol and oxygen at alcohol conversion conditions with a catalyst, said catalyst prepared by contacting an intimate mixture containing particles of a metal oxide support and particles of a catalytically active metal oxide of Groups VA, VIA, or VIIA with a gaseous stream containing an alcohol to cause said catalytically active metal oxide to form a monolayer of catalytically active metal oxide on said metal oxide support particles.

2. The method of claim 1 wherein said contacting of said intimate mixture is conducted at a temperature within the range from about 150°–600° C.

3. The method of claim 1 wherein said metal oxide support particles consist essentially of an oxide of a metal selected from the group consisting of titanium, tin, aluminum, zirconium, cerium, tantalum, niobium, and mixtures thereof.

4. The method of claim 3 wherein said catalytically active metal oxide particles comprise an oxide of a metal selected from the group consisting of vanadium, chromium, molybdenum, tungsten, and rhenium.

5. The method of claim 4 wherein said alcohol contains methanol, ethanol, propanol, or butanol.

6. The method of claim 1 wherein said metal oxide support particles consist essentially of titania, said catalytically active metal oxide comprises either molybdenum trioxide or vanadium pentoxide, and said alcohol comprises methanol.

7. The method of claim 5 wherein said oxide of molybdenum comprises molybdenum trioxide.

8. A method according to claim 1 wherein said reactant stream further contains an inert gas.

9. The method of claim 1 wherein said gaseous stream containing an alcohol also contains oxygen.

10. The method of claim 2 wherein said gaseous stream containing an alcohol also contains oxygen.

11. The method of claim 5 wherein said gaseous stream containing an alcohol also contains oxygen.

12. The method of claim 6 wherein said gaseous stream containing an alcohol also contains oxygen.

13. The method of claim 7 wherein said gaseous stream containing an alcohol also contains oxygen.

14. The method of claim 8 wherein said gaseous stream containing an alcohol also contains oxygen.

15. The method of claim 3 wherein said metal oxide support particles consist essentially of an oxide of a metal selected from the group consisting of titanium, tin, aluminum, zirconium, cerium, and mixtures thereof.

16. The method of claim 4 wherein said catalytically active metal oxide particles comprise an oxide of a metal selected from the group consisting of vanadium, chromium, molybdenum and rhenium.

17. The method of claim 15 wherein said gaseous stream containing an alcohol also contains oxygen.

18. The method of claim 16 wherein said gaseous stream containing an alcohol also contains oxygen.

19. A method for regenerating a spent catalyst whose activity for oxidizing an alcohol to an aldehyde in accordance with claim 1, has been degraded comprising contacting said spent catalyst with an oxygen-free gas flow of an alcohol and inert gas at a temperature within the range of from about 150° to 600° C. and thereafter contacting said spent catalyst with an alcohol-free gas stream containing oxygen and an inert gas.

* * * * *

UNITED STATES PATENT AND TRADEMARK OFFICE
CERTIFICATE OF CORRECTION

PATENT NO. : 6,350,918 B2  
DATED : February 26, 2002  
INVENTOR(S) : Israel E. Wachs et al.

It is certified that error appears in the above-identified patent and that said Letters Patent is hereby corrected as shown below:

Column 4,  
Line 45, "thereof" has been replaced with -- thereof. --.

Column 6,  
Line 20, "(4/16/80, ml/min" has been replaced with -- (4/16/80, ml/min) --.

Column 7,  
Line 8, "395 cm$_{-1}$" has been replaced with -- 395 cm$^{-1}$ --.

Column 10,  
Line 57, "FIG. 15$e$" has been replaced with -- FIG. 15$d$ --.

Column 11,  
Line 6, "mire" has been replaced with -- mixture --.

Column 12,  
Line 9, "support" has been replaced with -- support. --.

Column 13,  
Lines 4 and 5, "Dg=$g_{sg}$+$g_{as}$−$g_{ag}$<0" has been replaced with -- Dg= $g_{ag}$+$g_{as}$−$g_{sg}$<0 --.  
Line 40, "mire" has been replaced with -- mixture --.

Column 24,  
Line 14, "600º C." has been replaced with -- 600º C --.

Signed and Sealed this

Twenty-second Day of October, 2002

*Attest:*

*Attesting Officer*

JAMES E. ROGAN  
*Director of the United States Patent and Trademark Office*